United States Patent
Park et al.

(10) Patent No.: US 11,708,564 B2
(45) Date of Patent: Jul. 25, 2023

(54) MICROORGANISM EXPRESSING ACTIVE D-PROLINE REDUCTASE AND METHOD OF PRODUCING ACTIVE D-PROLINE REDUCTASE

(71) Applicant: CJ CheilJedang Corporation, Seoul (KR)

(72) Inventors: Jinseung Park, Seoul (KR); Bo Seong Park, Seoul (KR); Young Lyeol Yang, Seoul (KR); In Seok Oh, Seoul (KR); Nahum Lee, Seoul (KR); Jun Ok Moon, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 241 days.

(21) Appl. No.: 16/629,435

(22) PCT Filed: Jul. 12, 2018

(86) PCT No.: PCT/KR2018/007914
§ 371 (c)(1),
(2) Date: Jan. 8, 2020

(87) PCT Pub. No.: WO2019/013569
PCT Pub. Date: Jan. 17, 2019

(65) Prior Publication Data
US 2021/0317419 A1 Oct. 14, 2021

(30) Foreign Application Priority Data
Jul. 12, 2017 (KR) .................. 10-2017-0088632

(51) Int. Cl.
*C12N 9/02* (2006.01)
*C12P 13/00* (2006.01)
*C12N 15/70* (2006.01)

(52) U.S. Cl.
CPC ........... *C12N 9/0004* (2013.01); *C12N 15/70* (2013.01); *C12P 13/001* (2013.01); *C12Y 121/04001* (2013.01)

(58) Field of Classification Search
CPC ............................ C12N 9/0004; C12P 13/001
See application file for complete search history.

(56) References Cited

FOREIGN PATENT DOCUMENTS

KR 10-2015-0029526 A 11/2015

OTHER PUBLICATIONS

Studer. Residue mutations and their impact on protein structure and function: detecting beneficial and pathogenic changes. Biochem. J. (2013) 449, 581-594.*
GenBank: AM180355.1. prd operon. 2015.*
Lee et al., "Expression and post-translational modification of recombinant D-Proline reductase from Clostridium sticklandii in *Escherichia coli*," Abstract of Papers; ACS National Meeting & Exposition (2014).
Extended European Search Report issued in corresponding European Patent Application No. 18832792.8 dated Feb. 26, 2021.
(Continued)

*Primary Examiner* — Yong D Pak
(74) *Attorney, Agent, or Firm* — Morgan, Lewis & Bockius LLP

(57) ABSTRACT

The present disclosure relates to a microorganism expressing active D-proline reductase.

16 Claims, 11 Drawing Sheets

Specification includes a Sequence Listing.

(56) References Cited

OTHER PUBLICATIONS

Kabisch et al., "Identification of D-Proline Reductase from Clostridium sticklandii as a Selenoenzyme and Indications for a Catalytically Active Pyruvoyl Group Derived from a Cysteine Residue by Cleavage of a Proprotein," The Journal of Biological Chemistry, 274: 8445-8454 (1999).
GenBank: WP_003422102.1 (Apr. 14, 2017).
GenBank: OTF89550.1 (May 12, 2017).
GenBank: WP_003422104.1 (Oct. 27, 2016).
GenBank: WP_003702865.1 (Sep. 19, 2015).
GenBank: CBE06920.1 (Feb. 27, 2015).
GenBank: WP_080550217.1 (Mar. 30, 2017).
Jackson et al., "Analysis of Proline Reduction in the Nosocomial Pathogen Clostridium Difficile," Journal of Bacteriology, 188 (24): 8487-8495 (2006).
Wu et al., "The Clostridium difficile proline racemase is not essential for early logarithmic growth and infection," Canadian Journal of Microbiology, 60: 251-254 (2014).
Bouillaut et al., "Proline-Dependent Regulation of Clostridium difficile Strickland Metabolism," Journal of Bacteriology, 195(4): 844-854 (2013).
Bednarski et al., "In vitro processing of the proproteins GrdE of protein B of glycine reductase and PrdA of D-proline reductase from Clostridium sticklandii," European Journal of Biochemistry, 268: 3538-3544 (2001).
Itoh et al., "Decameric SelA-tRNASec Ring Structure Reveals Mechanism of Bacterial Selenocysteine Formation," Science, 340(6128): 75-78 (2013).
Su et al., "Selenocysteine insertion directed by the 3'-UTR SECIS element in *Escherichia coli*," Nucleic Acids Research, 33(8): 2486-2492 (2005).
Rudnick et al., "Reaction Mechanism and Structure of the Active Site of Proline Racemase," Biochemistry, 14(20): 4515-4522 (1975).
International Search Report issued in corresponding International Patent Application No. PCT/KR2018/007914 dated Nov. 2, 2018.
NCBI Reference Sequence WP_003422102.1; uncharacterized protein [Peptoclostridium difficile] (Jun. 8, 2016).
NCBI Reference Sequence WP_003702879.1; hypothetical protein [Lactobacillus salivarius] (May 13, 2013).
Fonknechten et al., "Clostridium sticklandii, a specialist in amino acid degradation: revisiting its metabolism through its genome sequence," BMC Genomics, 11: 555 (2010).
Office Action dated Feb. 22, 2023, issued in corresponding Chinese Patent Application No. 201880046286.3.

\* cited by examiner

[FIG. 1]
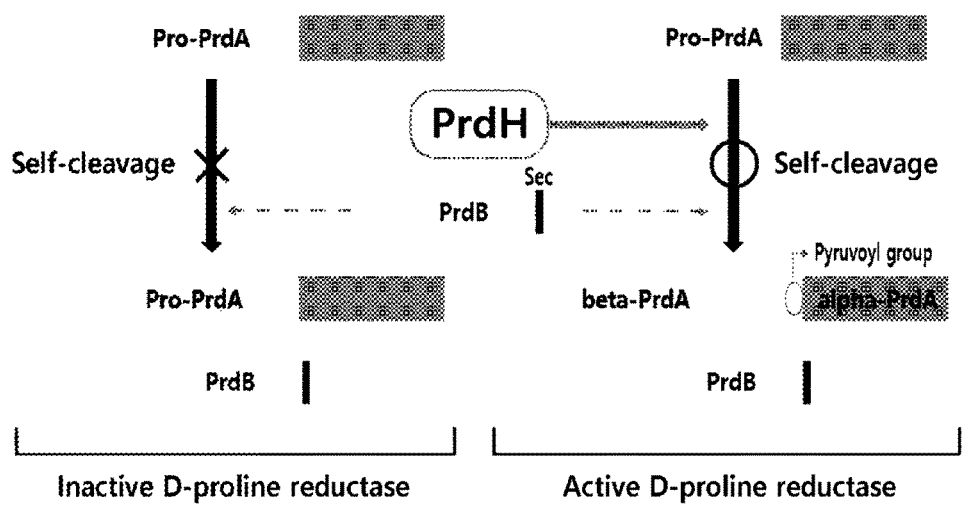

[FIG. 2]
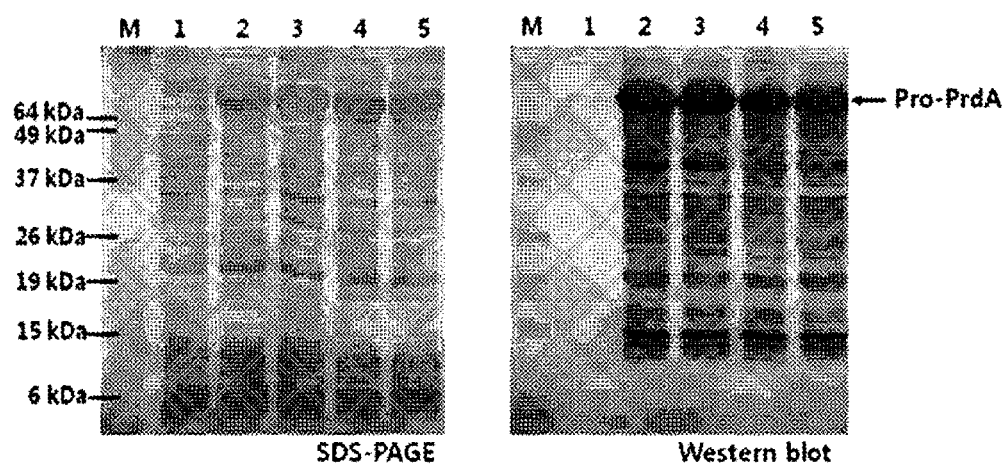
M: size marker (SeeBlue Plus2)
1 : No PrdA expression
2 : Wild-type PrdA
3 : PrdA (C421A)
4 : PrdA (10 mM DL-Proline added)
5 : PrdA + PrdH co-expression

[FIG. 3]
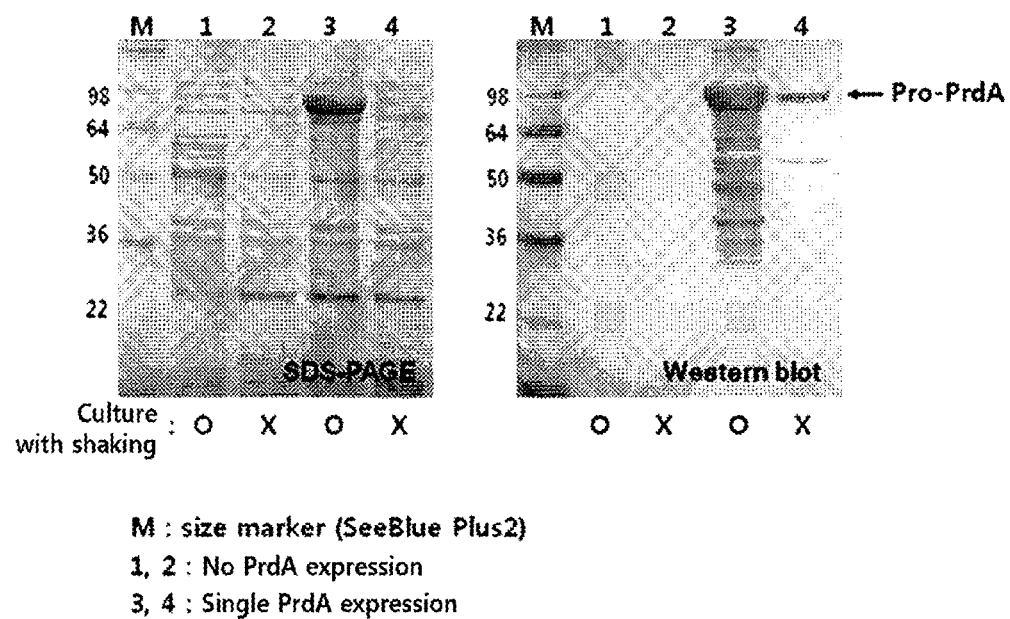

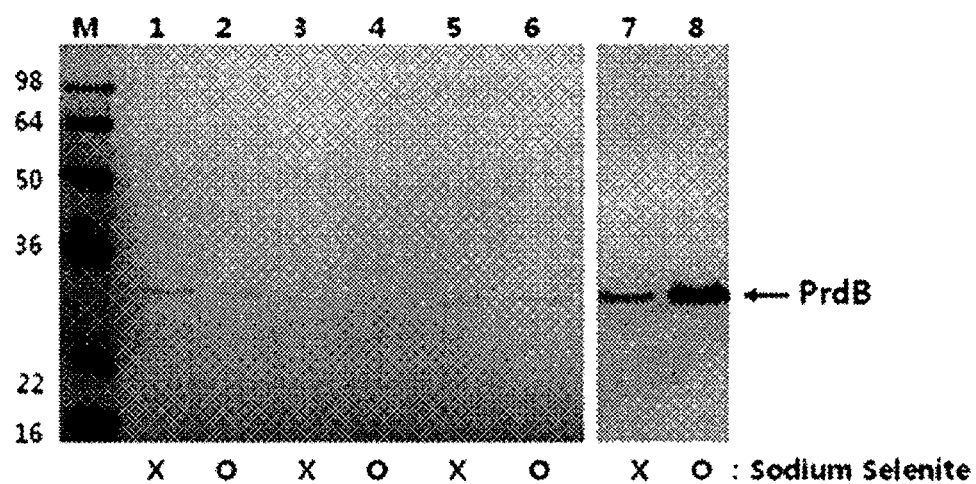
[FIG. 4]

[FIG. 5]
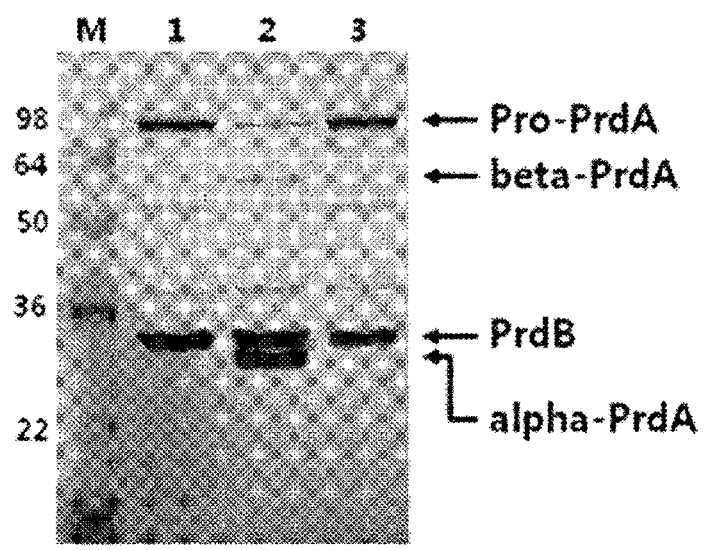
M: size marker (SeeBlue Plus2)
1 : PrdA + PrdB
2 : PrdA + PrdB + PrdH
3 : PrdA(C421A) + PrdB + PrdH

[FIG. 6]
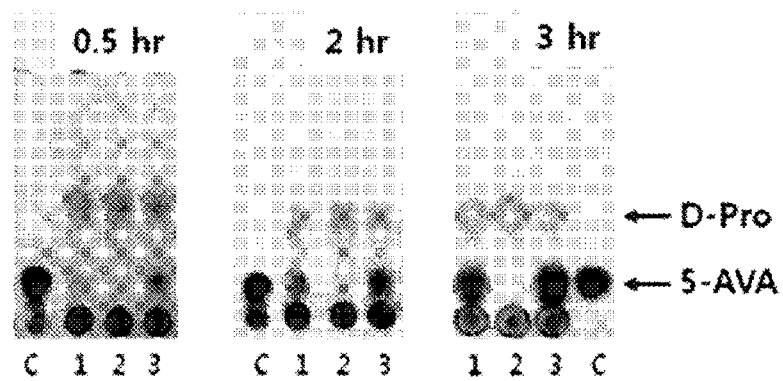
M: size marker (SeeBlue Plus2)
1 : PrdA + PrdB + PrdH
2 : PrdA + PrdB
3 : PrdA + PrdB + PrdH + PrdDEE$_2$
C : 5-aminovaleric acid

[FIG. 7]
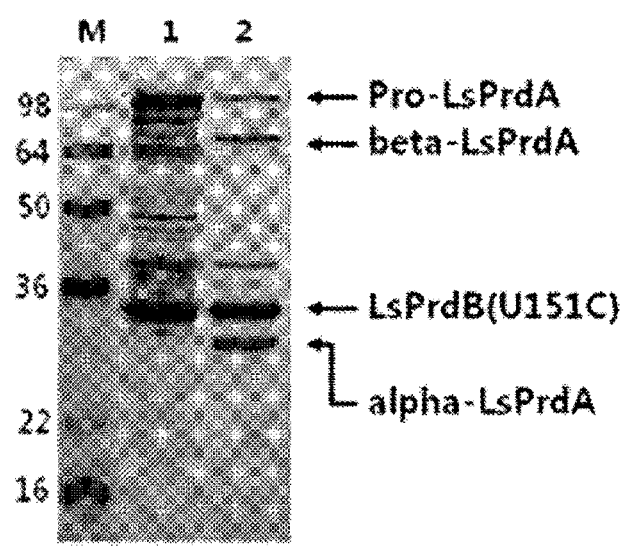
M: size marker (SeeBlue Plus2)
1 : LsPrdA + LsPrdB(U151C)
2 : LsPrdA + LsPrdB(U151C) + LsPrdH

[FIG. 8]
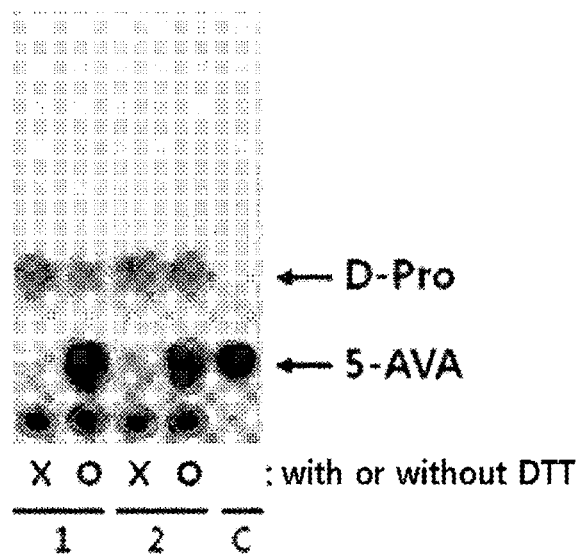
M: size marker (SeeBlue Plus2)
1 : PrdABH + PrdDEE$_2$
2 : PrdABH + PrdDEE$_2$ + PrdC
C : 5-aminovaleric acid

[FIG. 9]
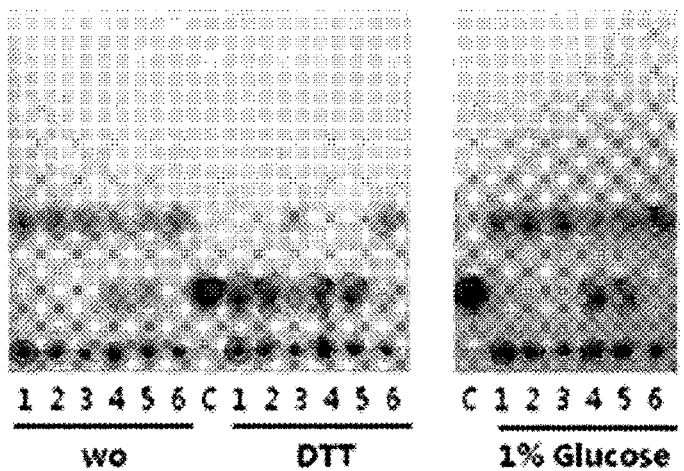
M: size marker (SeeBlue Plus2)
1 : PrdABH / whole cell
2 : PrdABH / cell lysate
3 : PrdABH / soluble fraction
4 : PrdABH + PrdCG / whole cell
5 : PrdABH + PrdCG / cell lysate
6 : PrdABH + PrdCG / soluble fraction
C : 5-aminovaleric acid

[FIG. 10]
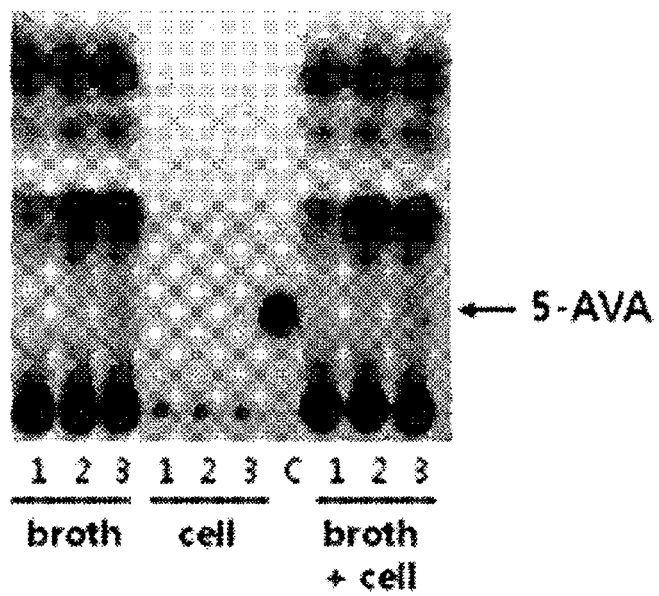
1 : BL21
2 : PrdABH + PrdCG
3 : PrdABH + PrdCG + PrdF
C : 5-aminovaleric acid

[FIG. 11]

(A) 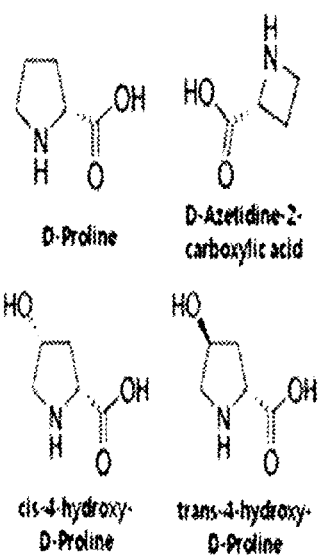

D-Proline

D-Azetidine-2-carboxylic acid cis-4-hydroxy-D-Proline trans-4-hydroxy-D-Proline (B) 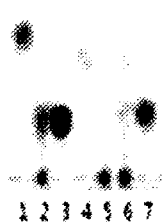

1 : D-Pro
2 : D-proline reductase + D-Pro
3 : 5-AVA
4 : D-Azetidine-2-carboxylic acid (D-Aze)
5 : D-proline reductase - No substrate added
6 : D-proline reductase + D-Aze
7 : γ-aminobutyric acid (GABA)

(C) 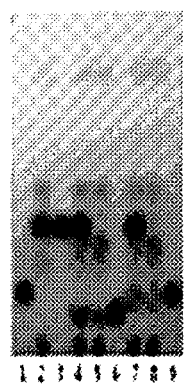

1 : D-Pro
2 : D-proline reductase + D-Pro
3 : 5-AVA
4 : D-proline reductase + D-Pro + cis-4-hydroxy-D-Proline
5 : D-proline reductase + cis-4-hydroxy-D-Proline
6 : cis-4-hydroxy-D-Proline
7 : D-proline reductase + D-Pro + trans-4-hydroxy-D-Proline
8 : D-proline reductase + trans-4-hydroxy-D-Proline
9 : trans-4-hydroxy-D-Proline

SEQUENCE LISTING

```
<160> NUMBER OF SEQ ID NOS: 26

<210> SEQ ID NO 1
<211> LENGTH: 94
<212> TYPE: PRT
<213> ORGANISM: Unknown
<220> FEATURE:
<223> OTHER INFORMATION: PrdH

<400> SEQUENCE: 1

Met Asp Arg Leu Lys Tyr Ile Ser Ser Glu Thr Phe Tyr Glu Gly Ile
1               5                   10                  15

Ile Val Asp Ile Lys Gly Gly Val Thr Ile Asp Leu Lys Gly Arg
            20                  25                  30

Leu Gly Gln Phe Lys Ile Pro Asn Arg Met Leu Ile Thr Asp Tyr Glu
        35                  40                  45

Leu Lys Ile Gly Gln Glu Val Gly Phe Met Leu Ser Tyr Pro Glu Val
    50                  55                  60

Leu Ser Pro Glu Pro Asn Gln Glu Tyr Val Glu Asn Ile Arg Arg Glu
65                  70                  75                  80

Lys Glu Lys Gln Ala Glu Met Gln Ser Lys Gln Glu Lys
                85                  90

<210> SEQ ID NO 2
<211> LENGTH: 285
<212> TYPE: DNA
<213> ORGANISM: Unknown
<220> FEATURE:
<223> OTHER INFORMATION: PrdH

<400> SEQUENCE: 2
atggataggt taaatatat ctcatcagag actttttatg aaggtattat agttgacatc      60
aaaggcggtg gagtgactat agacctaaaa ggtagacttg gacaatttaa aatacctaat     120
agaatgctta taactgacta cgaacttaag ataggtcaag aagttggatt catgctaagc     180
tatcctgagg tattaagtcc agagcctaat caagagtatg tagaaaatat taggagagaa     240
aaagaaaaac aagcagaaat gcaatcaaaa caagaagaaa ataa                      285

<210> SEQ ID NO 3
<211> LENGTH: 626
<212> TYPE: PRT
<213> ORGANISM: Unknown
<220> FEATURE:
<223> OTHER INFORMATION: PrdA

<400> SEQUENCE: 3

Met Ser Ile Thr Leu Glu Thr Ala Gln Ala His Ala Asn Asp Pro Ala
1               5                   10                  15

Val Cys Cys Cys Arg Phe Glu Ala Gly Thr Ile Ile Ala Pro Glu Asn
            20                  25                  30
```

-continued

```
Leu Glu Asp Pro Ala Ile Phe Ala Asp Leu Glu Asp Ser Gly Leu Leu
             35                  40                  45

Thr Ile Pro Glu Asn Gly Leu Thr Ile Gly Gln Val Leu Gly Ala Lys
 50                  55                  60

Leu Lys Glu Thr Leu Asp Ala Leu Ser Pro Met Thr Thr Asp Asn Val
 65                  70                  75                  80

Glu Gly Tyr Lys Ala Gly Ala Lys Glu Val Val Glu Glu Thr
                 85                  90                  95

Val Glu Glu Ala Ala Pro Val Ser Glu Ala Ala Val Val Pro Val Ser
                100                 105                 110

Thr Gly Val Ala Gly Glu Thr Val Lys Ile His Ile Gly Glu Gly Lys
                115                 120                 125

Asn Ile Ser Leu Glu Ile Pro Leu Ser Val Ala Gly Gln Ala Gly Val
            130                 135                 140

Ala Ala Pro Val Ala Asn Val Ala Ala Pro Val Ala Ser Ala Ala Ala
145                 150                 155                 160

Glu Val Ala Pro Lys Val Glu Glu Lys Lys Leu Leu Arg Ser Leu Thr
                165                 170                 175

Lys Lys His Phe Lys Ile Asp Lys Val Glu Phe Ala Asp Glu Thr Lys
                180                 185                 190

Ile Glu Gly Thr Thr Leu Tyr Ile Arg Asn Ala Glu Glu Ile Cys Lys
            195                 200                 205

Glu Ala Asn Glu Thr Gln Glu Leu Val Val Asp Met Lys Leu Glu Ile
            210                 215                 220

Ile Thr Pro Asp Lys Tyr Glu Thr Tyr Ser Glu Ala Val Leu Asp Ile
225                 230                 235                 240

Gln Pro Ile Ala Thr Lys Glu Glu Gly Glu Leu Gly Ser Gly Ile Thr
                245                 250                 255

Arg Val Ile Asp Gly Ala Val Met Val Leu Thr Gly Thr Asp Glu Asp
                260                 265                 270

Gly Val Gln Ile Gly Glu Phe Gly Ser Ser Gly Glu Leu Asn Thr
            275                 280                 285

Thr Ile Met Trp Gly Arg Pro Gly Ala Ala Asp Lys Gly Glu Ile Phe
290                 295                 300

Ile Lys Gly Gln Val Thr Ile Lys Ala Gly Thr Asn Met Glu Arg Pro
305                 310                 315                 320

Gly Pro Leu Ala Ala His Arg Ala Phe Asp Tyr Val Thr Gln Glu Ile
                325                 330                 335

Arg Glu Ala Leu Lys Lys Val Asp Asn Ser Leu Val Val Asp Glu Glu
            340                 345                 350

Val Ile Glu Gln Tyr Arg Arg Glu Gly Lys Lys Lys Val Val Val Ile
            355                 360                 365

Lys Glu Ile Met Gly Gln Gly Ala Met His Asp Asn Leu Ile Leu Pro
370                 375                 380

Val Glu Pro Val Gly Thr Leu Gly Ala Gln Pro Asn Val Asp Leu Gly
385                 390                 395                 400

Asn Met Pro Val Val Leu Ser Pro Leu Glu Val Leu Asp Gly Gly Ile
                405                 410                 415

His Ala Leu Thr Cys Ile Gly Pro Ala Ser Lys Glu Met Ser Arg His
            420                 425                 430

Tyr Trp Arg Glu Pro Leu Val Ile Arg Ala Met Glu Asp Glu Glu Ile
            435                 440                 445

Asp Leu Val Gly Val Val Phe Val Gly Ser Pro Gln Val Asn Ala Glu
```

```
              450             455             460
Lys Phe Tyr Val Ser Lys Arg Leu Gly Met Leu Val Glu Ala Met Glu
465                 470                 475                 480

Val Asp Gly Ala Val Val Thr Thr Glu Gly Phe Gly Asn Asn His Ile
                485                 490                 495

Asp Phe Ala Ser His Ile Glu Gln Ile Gly Met Arg Gly Ile Pro Val
                500                 505                 510

Val Gly Val Ser Phe Ser Ala Val Gln Gly Ala Leu Val Val Gly Asn
                515                 520                 525

Lys Tyr Met Thr His Met Val Asp Asn Asn Lys Ser Lys Gln Gly Ile
                530                 535                 540

Glu Asn Glu Ile Leu Ser Asn Asn Thr Leu Ala Pro Glu Asp Ala Val
545                 550                 555                 560

Arg Ile Met Ala Met Leu Lys Asn Ala Ile Glu Gly Val Glu Val Lys
                565                 570                 575

Ala Pro Glu Arg Lys Trp Asn Pro Asn Val Lys Leu Asn Asn Ile Glu
                580                 585                 590

Ala Ile Glu Lys Val Thr Gly Glu Lys Ile Val Leu Glu Glu Asn Glu
                595                 600                 605

Gln Ser Leu Pro Met Ser Lys Lys Arg Arg Glu Ile Tyr Glu Lys Asp
                610                 615                 620

Glu Asn
625

<210> SEQ ID NO 4
<211> LENGTH: 1881
<212> TYPE: DNA
<213> ORGANISM: Unknown
<220> FEATURE:
<223> OTHER INFORMATION: PrdA

<400> SEQUENCE: 4
atgtcaataa cttagaaac agctcaagcc catgcaaatg acccagcagt tgttgttgt        60 agatttgaag cgggaacaat tatagcgcca gaaaacttag aagatccagc aatatttgca      120
gacttagagg attctggatt attaacaata ccagaaaatg gattaactat aggtcaagta      180
ctaggagcta agttaaaaga aactttagat gcactttctc caatgactac agataacgta      240
gaaggataca aagcaggaga ggctaaagaa gaagtagtag aagaaacagt agaagaagca      300
gctccagtat cagaagcagc agtagttcca gtaagcacag gagttgcagg tgaaacagtt      360
aaaatacaca taggtgaagg taagaacata agcttagaga taccttatc agtagctggt       420 caagcaggag ttgctgctcc agtagcaaac gttgctgctc cagtggcaag tgcagcagca      480
gaagtagctc caaagttga agaaaagaa cttttaagaa gcttaactaa aaaacacttt        540
aaaatagata agttgaatt tgctgatgaa actaaaatag aaggaactac tttatacatc      600
agaaacgcag aagaaatatg taagaagct aatgaaactc aagagttagt tgtagatatg      660
aagttagaaa taataactcc tgataaatat gaaacttaca gtgaagctgt attagatata     720
caaccaatcg ctactaaaga agaaggcgaa ttaggttcag gtataactag agttatagat      780
ggagctgtaa tggtattaac tggtacagat gaagatggag ttcaaatagg tgaatttggt      840
tcttcagaag gtgagttaaa tactactata atgtggggta gaccaggtgc tgctgacaaa      900
ggtgaaatat tcatcaaagg tcaagtaaca ataaaagcag aactaacat ggaaagacca       960 ggacctttag ctgctcaccg tgcatttgac tatgtaactc aagaaataag agaagcatta     1020
```

-continued

```
aagaaagttg acaactcttt agtagttgat gaagaagtaa tagagcaata cagaagagaa      1080
ggtaaaaaga agttgttgt tataaaagaa ataatgggac aaggtgcaat gcatgataac       1140
ctaatattac cagttgagcc agttggtaca ttaggagctc aaccaaacgt tgacttagga      1200
aacatgccag ttgtattatc tccacttgaa gtattagatg gtggtatcca tgcattaact     1260
tgtataggac ctgcatcaaa agaaatgtca agacattact ggagagagcc attagtaata     1320
agagctatgg aagacgaaga aatagattta gtaggtgttg tatttgttgg ttctccacaa     1380
gtaaatgctg agaaattcta tgtatctaag agattaggta tgttagttga agctatggaa     1440
gttgatggag ctgtagtaac tactgaaggt ttcggaaaca accatataga tttcgcatct     1500
cacatagagc aaataggtat gagaggtata ccagtagttg gtgtaagttt ctcagctgtt     1560
caaggtgctc tagttgttgg taataaatac atgactcaca tggtagacaa caataagtct     1620
aagcaaggta tagagaatga aatattatct aacaacactt tagctccaga agatgctgtt    1680
agaataatgg ctatgcttaa aaatgctata gaaggtgtag aagttaaagc tcctgaaaga    1740
aaatggaatc caaatgttaa attaaataac atagaagcta tagaaaaagt tacaggagaa    1800
aaaatagtat tagaagagaa tgagcaatct ctaccaatga gtaagaagag aagagaaata    1860
tacgaaaaag acgaaaacta a                                               1881
```

<210> SEQ ID NO 5
<211> LENGTH: 240
<212> TYPE: PRT
<213> ORGANISM: Unknown
<220> FEATURE:
<223> OTHER INFORMATION: PrdB

<400> SEQUENCE: 5

```
Met Ser Leu Thr Thr Val Gln Gly Leu Gln Ser Glu Ile Phe Val Pro
1               5                   10                  15

Ile Thr Pro Pro Val Trp Thr Pro Val Thr Lys Glu Leu Lys Asp
            20                  25                  30

Met Thr Ile Ala Leu Ala Thr Ala Ala Gly Val His Leu Lys Ser Asp
        35                  40                  45

Lys Arg Phe Asn Leu Ala Gly Asp Thr Thr Phe Arg Ala Ile Pro Asn
    50                  55                  60

Thr Ala Thr Val Asp Glu Met Met Val Ser His Gly Gly Tyr Asp Asn
65                  70                  75                  80

Gly Asp Val Asn Lys Asp Ile Asn Cys Met Phe Pro Ile Asp Arg Leu
                85                  90                  95

His Glu Leu Ala Ala Glu Gly Phe Ile Lys Gly Val Ala Pro Met His
            100                 105                 110

Tyr Ala Phe Met Gly Gly Gly Gly Asn Gln His Val Phe Thr Glu Glu
        115                 120                 125

Thr Gly Pro Ala Ile Ala Ala Lys Leu Lys Glu Glu Gly Val Asp Gly
    130                 135                 140

Val Val Met Thr Ala Gly Gly Thr Cys His Arg Thr Ala Val Ile Val
145                 150                 155                 160

Gln Arg Ala Ile Glu Glu Ala Gly Ile Pro Thr Ile Ile Ala Ala
                165                 170                 175

Leu Pro Pro Val Val Arg Gln Asn Gly Thr Pro Arg Ala Val Ala Pro
            180                 185                 190

Leu Val Pro Met Gly Ala Asn Ala Gly Glu Pro His Asn Ile Glu Met
        195                 200                 205
```

```
Gln Thr His Ile Leu Arg Asp Thr Leu Glu Gln Leu Val Ala Ile Pro
    210                 215                 220

Ser Ala Gly Lys Ile Val Pro Leu Pro Tyr Glu Tyr Lys Ala His Val
225                 230                 235                 240

<210> SEQ ID NO 6
<211> LENGTH: 726
<212> TYPE: DNA
<213> ORGANISM: Unknown
<220> FEATURE:
<223> OTHER INFORMATION: PrdB

<400> SEQUENCE: 6
atgagcctta caacagtaca aggacttcaa tctgaaatat tcgttccaat aacacctcct      60
ccagtttgga ctcctgtaac taaagaatta aaagatatga ctatagcttt agctacagca    120
gctggtgttc atttaaaatc tgacaagaga tttaatctag caggagatac tacatttaga    180
gctataccta atacagctac agttgatgaa atgatggtat cacatggtgg atatgacaat    240
ggagatgtaa acaaagatat aaactgtatg ttccctatag atagattaca tgaattagct    300
gcagaaggat ttatcaaagg agtagctcct atgcactatg cattcatggg tggtggagga    360
aaccaacatg tcttcactga gaaactggt cctgctatcg ctgctaaact taggaagag     420 ggagtagacg gtgtagttat gacagctggc tgaggtactt gccatagaac tgccgtgatc    480
gtgcagagag caatagagga agctggaata cctacaataa taatagcagc tcttcctcca    540
gtagttagac aaaacggaac tcctagagca gttgctccat tagttccaat gggtgctaat    600
gctggtgaac cacataatat agaaatgcaa acacatatat taagagatac attagagcaa    660
ttagttgcaa taccatctgc tggtaagata gttccattac catacgaata taagctcac    720 gtttaa                                                               726

<210> SEQ ID NO 7
<211> LENGTH: 252
<212> TYPE: PRT
<213> ORGANISM: Unknown
<220> FEATURE:
<223> OTHER INFORMATION: PrdD

<400> SEQUENCE: 7
```

Met Glu Glu Lys Ile Met Arg Arg Leu Val Ile Lys Pro Phe His Met
1                   5                  10                  15

Asn Glu Val Asn Phe Gly Ser Lys Thr Ser Ile Lys Lys Asp Val Leu
                20                  25                  30

Thr Ile Asp Leu Ser Ser Ile Asp Glu Ile Lys Glu Arg Glu Glu Leu
            35                  40                  45

Ile Thr Asp Ile Lys Val Asp Ile Ile Lys Pro Gly Asp Tyr Asp Arg
        50                  55                  60

Glu Ile Asn Thr Ile Met Asp Ile Ile Pro Ile Ser Thr Lys Val Leu
65                  70                  75                  80

Gly Arg Leu Gly Glu Gly Ile Thr His Thr Leu Thr Gly Val Tyr Val
                85                  90                  95

Met Leu Thr Gly Ala Asp Glu Asp Gly Asn Gln Met His Glu Phe Gly
                100                 105                 110

Ser Ser Glu Gly Ile Leu Lys Asp Gln Met Val Phe Gly Arg Tyr Gly
            115                 120                 125

Thr Pro Ser Val Glu Asp Tyr Ile Ile His Val Asp Val Thr Leu Lys
        130                 135                 140

```
Gly Gly Leu Pro Phe Glu Arg Thr Leu Pro Leu Ala Ala Phe Arg Ala
145                 150                 155                 160

Cys Asp Asp Phe Ile Gln Glu Ile Arg Ala Ser Leu Lys Met Glu Asp
                165                 170                 175

Gly Arg Asn Ala Thr Gln Val Arg Glu Tyr Phe Asp Lys Ile Arg Pro
            180                 185                 190

Asn Ala Lys Lys Val Val Ile Val Lys Gln Ile Ala Gly Gln Gly Ala
        195                 200                 205

Met Tyr Asp Asn Gln Leu Phe Ser Lys Glu Pro Ser Gly Phe Glu Gly
    210                 215                 220

Gly Thr Ser Ile Ile Asp Met Gly Asn Val Pro Met Ile Ile Ser Pro
225                 230                 235                 240

Asn Glu Tyr Arg Asp Gly Ala Leu Arg Ala Met Thr
                245                 250

<210> SEQ ID NO 8
<211> LENGTH: 759
<212> TYPE: DNA
<213> ORGANISM: Unknown
<220> FEATURE:
<223> OTHER INFORMATION: PrdD

<400> SEQUENCE: 8
atggaagaaa aaataatgag aagacttgtt ataaaaccgt tcatatgaa tgaagttaat       60
ttcggttcaa aacttctat aaagaaagat gtacttacaa tagatttatc aagtatagat     120
gaaataaaag aaagagaaga gttaataaca gacataaaag tagacattat aaaacctgga     180
gattatgaca gagaaattaa tactattatg gacattatac caatatcaac aaaagtttta     240
ggcagactgg gagagggtat tacacatact ttaacgggtg tatatgtaat gttaactggt     300
gcagatgaag atggaaatca aatgcatgaa tttggttctt cagaaggaat tttgaaagac     360
caaatggtat ttgggagata tggaactcca tcagttgaag attatataat ccatgtagat     420
gtaactttaa agggaggttt acctttgaa agaacacttc cacttgcagc attcagagca     480
tgtgatgatt ttatacaaga aataagagca tctttgaaaa tggaagacgg aagaaatgct     540
actcaagttc gtgaatattt tgacaaaatt cgaccaaatg caaaaaaggt tgtcatagta     600
aaacaaatag caggtcaagg tgctatgtat gacaatcagt tattctcaaa ggaacctagt     660
ggatttgaag gaggaacatc aattatagat atgggaaatg tacctatgat tatatctcct     720
aatgaataca gagatggtgc ccttagagct atgacttaa                             759

<210> SEQ ID NO 9
<211> LENGTH: 155
<212> TYPE: PRT
<213> ORGANISM: Unknown
<220> FEATURE:
<223> OTHER INFORMATION: PrdE

<400> SEQUENCE: 9

Met Gly Ile Gly Pro Ser Thr Lys Glu Thr Ser Leu His His Phe Arg
1               5                   10                  15

Asp Pro Leu Leu Asp Ile Val Glu Ser Asp Lys Asp Val Asp Leu Leu
            20                  25                  30

Gly Val Ile Val Val Gly Thr Pro Asp Gly Asn Glu Asn Lys Thr Phe
        35                  40                  45

Val Gly Gln Arg Thr Ala Ala Trp Leu Glu Ala Met Arg Val Asp Gly
    50                  55                  60
```

```
Ala Ile Val Ser Ser Asp Gly Trp Gly Asn Ser His Val Asp Tyr Ala
 65                  70                  75                  80

Asn Thr Phe Glu Glu Ile Gly Lys Arg Asp Ile Pro Val Gly Val
                 85                  90                  95

Thr Phe Asn Gly Thr Gln Ala Lys Phe Val Val Ser Asn Gln Tyr Met
            100                 105                 110

Asp Thr Ile Val Asp Met Asn Lys Ser Lys Glu Gly Ile Glu Thr Glu
        115                 120                 125

Val Val Gly Glu Asn Asn Thr Asn Glu Ile Asp Ala Lys Lys Ala Leu
    130                 135                 140

Ala Phe Leu Lys Leu Lys Met Arg Lys His Gly
145                 150                 155
```

<210> SEQ ID NO 10
<211> LENGTH: 468
<212> TYPE: DNA
<213> ORGANISM: Unknown
<220> FEATURE:
<223> OTHER INFORMATION: PrdE

<400> SEQUENCE: 10

```
atgggaatag gaccttcaac aaaagaaaca tctcttcatc actttagaga cccactttta      60
gacatagttg aaagtgataa ggatgtagat ttacttggag taatagtagt aggaactcca     120
gatgaaaatg aaaataaaac ctttgtggga caaagaacgg ccgcttggct ggaagccatg     180
agagtagatg gagctatagt ttcatcagat ggttggggaa actcacatgt tgactacgct     240
aacacatttg aggaaatagg aaaaagagat atacctgtag ttggagttac atttaatggg     300
actcaagcta agtttgttgt aagcaatcaa tatatggata ccatagttga tatgaacaaa     360
tcaaaagaag gtattgagac agaagtagtt ggagaaaaca acacaaatga aatagatgct     420
aaaaaagctt tggcattttt aaaacttaaa atgagaaaac atggataa                  468
```

<210> SEQ ID NO 11
<211> LENGTH: 160
<212> TYPE: PRT
<213> ORGANISM: Unknown
<220> FEATURE:
<223> OTHER INFORMATION: PrdE2

<400> SEQUENCE: 11

```
Met Ser Phe Val Gly Ile Ser Thr Ser Met Lys Asn Thr Ser Leu His
  1               5                  10                  15

Ile Phe Arg Asp Pro Leu Leu Asp Leu Ile Asp Asn Asp Ser Asp Ile
                 20                  25                  30

Asp Leu Leu Gly Val Val Val Gly Thr Ser Glu His Asn Glu Trp
             35                  40                  45

Lys Thr Phe Leu Ala Thr Arg Leu Gly Arg Trp Ile Glu Ser Leu Arg
 50                  55                  60

Pro Asp Gly Val Ile Ile Thr Leu Asp Met Ala Gly Asn Gln His Ile
 65                  70                  75                  80

Asp Phe Thr Asn Ala Ile Ala Glu Phe Val Lys Ser Asp Ile Pro Thr
                 85                  90                  95

Val Gly Leu Thr Ile Met Gly Ala Asp Gly Leu Val Ile Thr Asn Pro
            100                 105                 110

Tyr Leu Asp Lys Ala Thr Ile Ile Asp Tyr Lys Lys Thr Thr Gly Tyr
        115                 120                 125

Ile Glu Thr Glu Val Val Gly Asp Asn His Met Asp Glu Val Asp Val
```

```
                130              135              140
Lys Lys Ala Leu Ala Phe Leu Lys Leu Lys Met Arg Lys Asp Ala Lys
145                 150                 155                 160

<210> SEQ ID NO 12
<211> LENGTH: 483
<212> TYPE: DNA
<213> ORGANISM: Unknown
<220> FEATURE:
<223> OTHER INFORMATION: PrdE2

<400> SEQUENCE: 12
atgagttttg tgggaatttc tacatcaatg aaaaacacat cacttcatat atttagagac    60
ccgttactag atttgataga taatgattct gacatagact tgttaggagt ggttgtagtt   120
gggacatcag agcacaatga atggaaaaca tttttagcaa ctagacttgg aagatggatt   180
gaatcattgc gacctgatgg agtgattata actttagata tggcaggaaa ccagcacatt   240
gattttacaa atgctatagc agagtttgta aaatcagata tacctacagt aggtcttact   300
attatgggag cagatggatt agtaattacc aatccatatt tggataaagc taccataatt   360
gattataaaa agacaacagg ctacatgaaa acagaagtag ttggagacaa tcacatggac   420
gaagttgatg ttaaaaaagc attggctttc ctaaaattaa aaatgcgtaa agacgcaaaa   480
taa                                                                 483

<210> SEQ ID NO 13
<211> LENGTH: 437
<212> TYPE: PRT
<213> ORGANISM: Unknown
<220> FEATURE:
<223> OTHER INFORMATION: PrdC

<400> SEQUENCE: 13

Met Asn Lys Leu Tyr Ser Ile Leu Leu Lys Gln His Val Gly Gly Pro
1               5                   10                  15

Asp Lys Pro Val Val Ser Val Gly Asp Val Val Lys Lys Gly Thr Leu
                20                  25                  30

Ile Ala Glu Pro Thr Gly Leu Gly Ala Asn Ile Tyr Ala Ser Val Ser
            35                  40                  45

Gly Lys Ile Ser Glu Ile Asn Asp Gln Ala Ile Val Ile Glu Ala Asp
        50                  55                  60

Glu Val Gln Glu Asp Thr Phe Glu Pro Leu Lys Gly Glu Gly Ile Leu
65                  70                  75                  80

Asp Leu Ile Lys Glu Ala Gly Val Val Gly Met Gly Gly Ala Gly Phe
                85                  90                  95

Pro Thr His Val Lys Leu Asn Ile Asp Leu Asn Gly Gly Thr Ile Leu
            100                 105                 110

Ala Asn Ala Ala Glu Cys Glu Pro Leu Leu Ala His Asn Ile Lys Glu
        115                 120                 125

Ile Glu Glu Arg Pro Glu Ile Val Tyr Gln Gly Ile Lys Tyr Ala Met
    130                 135                 140

Glu Val Thr Asn Ala Gly Lys Gly Met Leu Ala Ile Lys Ser Lys His
145                 150                 155                 160

Pro Lys Ala Ile Glu Ala Phe Lys Lys Val Ile Lys Pro Gly Asp Asn
                165                 170                 175

Ile Glu Val Ala Glu Leu Val Asp Met Tyr Pro Met Gly Glu Glu Arg
            180                 185                 190
```

Ala Ile Val Arg Asp Val Leu Gly Lys Leu Leu Glu Pro Thr Gln Leu
            195                 200                 205

Pro Ser Glu Ala Asn Ala Val Val Ile Asn Val Glu Thr Leu Thr Arg
    210                 215                 220

Ile Val Glu Ala Val Glu Gln Lys Arg Pro Val Ile Ser Lys Asn Ile
225                 230                 235                 240

Thr Val Val Gly Gln Leu Asn Ser Gly Lys Glu Ser Ile Val Phe Glu
                245                 250                 255

Asp Val Pro Ile Gly Thr Thr Val Gly Glu Leu Ile Glu Arg Ala Gly
            260                 265                 270

Gly Ile Lys Gly Glu Tyr Gly Glu Ile Leu Gly Gly Pro Phe Thr
        275                 280                 285

Gly Lys Ala Thr Thr Leu Asp Ala Pro Ile Thr Lys Thr Ser Gly Gly
    290                 295                 300

Ile Ile Val Thr Met Pro Phe Val Asn Glu Lys Arg Lys Met Gly Leu
305                 310                 315                 320

Leu Val Cys Ala Cys Gly Pro Asn Glu Glu Arg Met Arg Asp Ile Ala
                325                 330                 335

Thr Lys Met Gly Val Thr Asp Ile Val Ser Val Gln Lys Cys Lys Gln
            340                 345                 350

Ala Gln Glu Ile Lys Gly Ala Leu Lys Cys Glu Asn Pro Gly His Cys
        355                 360                 365

Pro Gly Gln Ala Gln Lys Cys Ile Glu Phe Lys Lys Ala Gly Ala Glu
    370                 375                 380

Val Ile Leu Ile Gly Asn Cys Thr Asp Cys Ser Asn Thr Val Met Gly
385                 390                 395                 400

Ser Ala Pro Lys Leu Lys Leu Gly Val Tyr His Ile Thr Asp His Val
                405                 410                 415

Met Arg Thr Val Asn His Pro Leu Ile Arg Arg Ile Lys Gly Asp Val
            420                 425                 430

Arg Leu Lys Ile Lys
        435

<210> SEQ ID NO 14
<211> LENGTH: 1314
<212> TYPE: DNA
<213> ORGANISM: Unknown
<220> FEATURE:
<223> OTHER INFORMATION: PrdC

<400> SEQUENCE: 14
ttgaacaaac tatattctat tttattaaaa caacacgttg gtggtccaga taagccagta      60
gtaagtgttg agatgtagt aaaaaaagga actctaatcg cagaaccaac tggattaggg     120
gcaaatattt atgccagtgt tagtggaaaa ataagtgaaa taaatgacca agcgatagta     180
attgaagctg atgaagtaca agaagatact tttgaaccat aaaaggaga aggtatactt     240 gacttaatta agaagctgg agtagtagga atgggtggag caggattccc tactcatgta     300
aaattaaaca tagatttaaa tggtggaaca atattagcaa atgcagctga atgtgaacct     360
ttattagctc ataatataaa agaaatagaa gaaagaccag aaatagttta tcaaggtata     420
aaatatgcta tggaagttac taatgctgga aaaggtatgc tagcaataaa aagtaagcat     480
ccaaaagcaa tagaagcttt caaaaaagta ataaagccag agacaacat agaagttgca     540 gaactagttg atatgtaccc aatgggagaa gagagagcaa tagtaagaga cgttctagga     600
aaattacttg agccaactca attaccttca gaggctaatg cagtagtaat aaacgtagaa     660

```
acactaacta gaatagtaga ggctgttgag caaaaaagac cagttatatc taaaaatata    720
actgtagttg gtcaattaaa cagtggaaaa gaatctatag tgtttgaaga tgtgccaatt    780
ggaacaactg tcggagaatt aattgaaaga gctggtggaa taaaaggtga atatggtgaa    840
ataatcctag gaggaccttt cactggtaaa gctactactt tagatgctcc aataactaaa    900
actagtggtg gtataatagt tactatgcca tttgttaatg aaaagagaaa atgggtctt    960 ttagtttgtg catgtggacc taatgaagaa agaatgagag atatagcaac taaaatggga    1020
gttactgata tagtatcagt tcaaaaatgt aaacaagctc aagaaattaa aggtgcatta    1080
aaatgtgaaa atccaggaca ctgtccagga caagctcaaa atgtattga atttaagaaa     1140 gctggagcag aagttatatt aataggaaac tgtactgact gtagtaacac agtaatgggt    1200
tctgcaccaa aattaaaatt aggtgtatat catattactg accatgtaat gagaacagtt    1260
aatcacccat taataagaag aataaaaggt gacgtaagat taaaaataaa ataa          1314
```

<210> SEQ ID NO 15
<211> LENGTH: 293
<212> TYPE: PRT
<213> ORGANISM: Unknown
<220> FEATURE:
<223> OTHER INFORMATION: PrdG

<400> SEQUENCE: 15

```
Met Val Ala Ile Leu Lys Ala Leu Tyr Val Val Phe Ala Ala Ile Phe
1               5                   10                  15

Ala Val Val Phe Gly Lys Asp Val Ala Lys Ala Asn Lys Glu Gly Lys
                20                  25                  30

Leu Glu Glu Gln Ser Thr Pro Lys Val Ala Val Thr Gly Phe Ile Thr
            35                  40                  45

Asp Phe Phe Asp Thr Leu Gly Ile Gly Ser Phe Ala Pro Thr Ile Ala
        50                  55                  60

Met Ser Lys Ala Leu Lys Leu Asn Ile Pro Asp Lys Lys Met Pro Gly
65                  70                  75                  80

Thr Leu Asn Val Ala His Thr Ile Pro Val Val Thr Glu Ala Phe Ile
                85                  90                  95

Phe Thr Ser Ile Ile Pro Val Asp Gly Val Thr Leu Val Ser Met Val
                100                 105                 110

Val Ala Ala Ala Val Gly Ser Tyr Ile Gly Ala Gly Ile Ile Ala Lys
            115                 120                 125

Met Asp Glu Arg Lys Ile Gln Leu Val Met Gly Val Thr Leu Ala Leu
        130                 135                 140

Thr Ala Ile Leu Met Leu Leu Gly His Pro Trp Ile Asn Val Leu Pro
145                 150                 155                 160

Gly Gly Gly Asn Glu Leu Gly Leu Thr Gly Val Lys Leu Val Ile Gly
                165                 170                 175

Val Ile Gly Asn Phe Ile Leu Gly Ala Leu Met Thr Ala Gly Ile Gly
            180                 185                 190

Leu Tyr Ala Pro Gly Met Ala Met Val Tyr Phe Leu Gly Met Ser Ala
        195                 200                 205

Lys Val Ala Phe Pro Ile Val Met Gly Ser Cys Ala Leu Leu Met Pro
        210                 215                 220

Val Ala Ser Met Lys Phe Ile Lys Glu Asp Ala Tyr Thr Lys Lys Ala
225                 230                 235                 240

Ser Val Ile Ile Ala Ile Cys Gly Leu Ile Gly Val Phe Val Ala Ala
```

245                 250                 255
Tyr Ile Val Lys Thr Leu Pro Met Asp Ile Leu Lys Ala Leu Val Ile
            260                 265                 270

Val Val Ile Ala Tyr Thr Ser Ala Thr Met Ile Met Ala Ala Asn Lys
            275                 280                 285

Asn Lys Lys Thr Ala
        290

<210> SEQ ID NO 16
<211> LENGTH: 882
<212> TYPE: DNA
<213> ORGANISM: Unknown
<220> FEATURE:
<223> OTHER INFORMATION: PrdG

<400> SEQUENCE: 16

```
atggtagcaa tcttaaaggc attatatgta gtattcgcag caatctttgc agttgtgttt      60
ggtaaagacg tagctaaagc aaacaaagag gggaaactag aagaacaaag tactccaaaa     120
gttgctgtaa caggatttat aacagacttc tttgatacat taggaatagg gtcatttgct     180
ccaacaatag caatgtcaaa ggctttaaag ttaaatatac cagataaaaa aatgcctggt     240
acattaaacg tagcacatac tattccagtt gttacagaag cattcatatt tacatcaatc     300
ataccagttg atggtgttac tttagtatct atggttgtgg cagcagcagt tggttcatat     360
ataggtgcag gaataatagc taagatggac gagagaaaaa tacaacttgt tatgggtgta     420
acttagcat taacagcaat attaatgtta ttaggtcatc cttggattaa cgtattacca     480
ggtggaggaa atgaattagg tcttactggt gttaaattag taataggtgt aataggtaac     540
tttatactag gagctttaat gacagctggt ataggtctat atgctccagg tatggcaatg     600
gtttatttct taggaatgtc tgcaaaagtt gcattcccaa tagttatggg ttcttgtgca     660
ttattaatgc cagttgcaag tatgaaattc ataaaagaag atgcatatac taaaaaagca     720
tcagttataa tagctatatg tggtttaata ggagttttcg tagctgcata tagtaaaaa     780
actctaccaa tggatatatt aaaagcatta gtaatagtag ttatagctta tacttctgct     840
acaatgataa tggctgcaaa taaaaacaaa aagactgctt ag                        882
```

<210> SEQ ID NO 17
<211> LENGTH: 335
<212> TYPE: PRT
<213> ORGANISM: Unknown
<220> FEATURE:
<223> OTHER INFORMATION: PrdF

<400> SEQUENCE: 17

Met Lys Phe Ser Arg Ser Ile Gln Ala Ile Asp Ser His Thr Ala Gly
1               5                   10                  15

Glu Ala Thr Arg Ile Val Val Gly Gly Ile Pro Asn Ile Lys Gly Asn
            20                  25                  30

Ser Met Pro Glu Lys Lys Glu Tyr Leu Glu Glu Asn Leu Asp Tyr Leu
        35                  40                  45

Arg Thr Ala Ile Met Leu Glu Pro Arg Gly His Asn Asp Met Phe Gly
    50                  55                  60

Ser Val Met Thr Gln Pro Cys Cys Pro Asp Ala Asp Phe Gly Ile Ile
65                  70                  75                  80

Phe Met Asp Gly Gly Gly Tyr Leu Asn Met Cys Gly His Gly Thr Ile
            85                  90                  95

```
Gly Ala Met Thr Ala Ala Ile Glu Thr Gly Val Val Pro Ala Val Glu
                100                 105                 110

Pro Val Thr His Val Val Met Glu Ala Pro Ala Gly Ile Ile Arg Gly
            115                 120                 125

Asp Val Thr Val Val Asp Gly Lys Ala Lys Glu Val Ser Phe Leu Asn
        130                 135                 140

Val Pro Ala Phe Leu Tyr Lys Glu Gly Val Glu Val Asp Leu Pro Gly
145                 150                 155                 160

Val Gly Thr Val Lys Phe Asp Ile Ser Phe Gly Ser Phe Phe Ala
                165                 170                 175

Ile Ile His Ala Ser Gln Leu Gly Leu Lys Ile Glu Pro Gln Asn Ala
                180                 185                 190

Gly Lys Leu Thr Glu Leu Ala Met Lys Leu Arg Asp Ile Ile Asn Glu
            195                 200                 205

Lys Ile Glu Ile Gln His Pro Thr Leu Ala His Ile Lys Thr Val Asp
        210                 215                 220

Leu Val Glu Ile Tyr Asp Glu Pro Thr His Pro Glu Ala Thr Tyr Lys
225                 230                 235                 240

Asn Val Val Ile Phe Gly Gln Gly Gln Val Asp Arg Ser Pro Cys Gly
                245                 250                 255

Thr Gly Thr Ser Ala Lys Leu Ala Thr Leu His Ala Lys Gly Glu Leu
            260                 265                 270

Lys Val Gly Glu Lys Phe Val Tyr Glu Ser Ile Leu Gly Thr Leu Phe
        275                 280                 285

Lys Gly Glu Ile Val Glu Thr Lys Val Ala Asp Phe Asn Ala Val
290                 295                 300

Val Pro Lys Ile Thr Gly Ser Ala Tyr Ile Thr Gly Phe Asn His Phe
305                 310                 315                 320

Val Ile Asp Glu Glu Asp Pro Leu Lys His Gly Phe Ile Leu Lys
                325                 330                 335

<210> SEQ ID NO 18
<211> LENGTH: 1008
<212> TYPE: DNA
<213> ORGANISM: Unknown
<220> FEATURE:
<223> OTHER INFORMATION: PrdF

<400> SEQUENCE: 18
atgaaattta gcagaagtat acaagctata gactctcata cagcaggtga agcaactaga      60
atagttgtag gtggaatacc taacataaaa ggaaattcta tgcctgagaa aaagaatat     120 ttagaggaaa atctagatta tttaagaact gctataatgt tagagccaag aggacataat    180
gatatgtttg ttctgtaat gactcaacct tgttgcccag atgctgactt tggaataatc     240
ttcatggatg gtggcggata ccttaacatg tgtggccatg gtacaatagg agctatgaca    300
gcagctatat aaacaggtgt agttccagca gtagagcctg taactcatgt agttatggaa    360
gctccagcag gaataataag aggagacgtt acagttgtag atggaaaagc taagaagta    420 tcattcttaa acgtaccagc tttcttatat aaagaaggtg ttgaagttga cttaccaggt    480
gttggaactg ttaaatttga catatcattt ggtggaagct ctttgctat aatacatgca    540 agtcaattag gtttaaaaat cgaacctcaa atgctggta aattaactga actagctatg    600
aaacttagag atataataaa tgagaaaata gaaatacaac atccaacttt agctcatata    660
aaaactgtag acttagttga aatatatgat gagccaactc atccagaagc tacttacaaa    720
```

-continued

```
aatgtagtta tatttggtca aggtcaagtt gacagatctc catgtggaac tggaacaagt    780
gctaaattag ctactttaca tgctaaaggt gaattaaaag taggagaaaa attcgtatat    840
gaaagtatat taggaacttt attcaaaggt gaaatagttg aagaaactaa agttgcagat    900
ttcaatgctg tagtacctaa ataactggt tctgcttata taactggatt taatcatttt    960
gtaatagatg aagaagaccc acttaaacat ggatttattc ttaaataa                1008
```

<210> SEQ ID NO 19
<211> LENGTH: 634
<212> TYPE: PRT
<213> ORGANISM: Lactobacillus salivarius
<220> FEATURE:
<221> NAME/KEY: PEPTIDE
<222> LOCATION: (1)..(634)
<223> OTHER INFORMATION: PrdA(LsPrdA)

<400> SEQUENCE: 19

```
Met Ser Ile Ser Val Glu Gln Ala Lys Glu His Ala Lys Asp Pro Ala
1               5                   10                  15

Val Leu Cys Cys Arg Arg Glu Ala Gly Lys Val Leu Glu Ala Ala Asp
            20                  25                  30

Phe Glu Asp Pro Thr Leu Phe Asp Asp Tyr Val Ser Ser Gly Leu Leu
        35                  40                  45

Glu Ile Pro Glu Asp Thr Leu Thr Ile Glu Gln Ala Leu Gly Ala Thr
    50                  55                  60

Leu Asn Thr Thr Thr Asp Ala Leu Asn Pro Leu Val Pro Gly Ile Val
65                  70                  75                  80

Asp Asn Ile Gln Gly Asn Glu Glu Ala Ser Ser Asp Lys Asp Glu
                85                  90                  95

Asn Val Glu Glu Glu Thr Pro Val Val Ala Glu Ala Asn Asn Glu Val
            100                 105                 110

Val Asn Ser Thr Ser Ser Asn Gly Thr Phe His Leu Arg Ile Ala Lys
        115                 120                 125

Gly Glu Gly Ile Asp Leu Glu Ile Pro Leu Asp Val Leu Lys Lys Asn
    130                 135                 140

Thr Ala Asn Ser Ala Val Asp Val Pro Lys Ala Glu Thr Ser Ala Asp
145                 150                 155                 160

Val Thr Asn Lys Asp Val Ala Glu Asp Glu Glu Ser Ala Glu Asp Ala
                165                 170                 175

Lys Val Val Arg Thr Leu Thr Lys Lys Tyr Phe Lys Val Asp Glu Val
            180                 185                 190

Lys Phe Gly Asp Thr Thr Lys Phe Asp Gly Thr Thr Leu Tyr Leu Arg
        195                 200                 205

Asn Pro Lys Glu Leu Cys Lys Glu Ala Val Asp Thr Glu Ala Ile Val
    210                 215                 220

Lys Gly Met Glu Ile Glu Ile Thr Pro Asp Asp Tyr Ser Asn Tyr
225                 230                 235                 240

Ser Asn Thr Ile Met Asp Val Gln Pro Ile Ala Thr Lys Glu Gly Asp
                245                 250                 255

Ser Asp Leu Gly Val Gly Val Thr Lys Val Val Asp Gly Ala Val Val
            260                 265                 270

Val Leu Thr Gly Thr Asp Glu Asn Gly Val Gln Val Gly Glu Phe Gly
        275                 280                 285

Ser Ser Glu Gly Pro Leu Asn Glu Asn Ile Met Trp Asn Arg Pro Gly
    290                 295                 300
```

```
Ala Val Asp Lys Gly Glu Ile Met Ile Lys Ile Asp Val Val Ile Glu
305                 310                 315                 320

Ala Gly Thr Asn Arg Glu Arg Lys Gly Pro Leu Gly Ala His Leu Ala
            325                 330                 335

Ala Asp Tyr Ile Thr Gln Glu Ile Arg Glu Ala Leu Lys Asp Val Asp
                340                 345                 350

Asp Ser Ser Ala Val Arg Thr Glu Glu Phe Val Gln Lys Arg His Pro
            355                 360                 365

Lys Gln Lys Arg Val Leu Ile Val Lys Glu Ile Met Gly Gln Gly Ala
370                 375                 380

Met His Asp Asn Leu Ile Met Pro Val Glu Pro Val Gly Thr Leu Gly
385                 390                 395                 400

Ala Lys Pro Asn Val Asp Leu Gly Asn Leu Pro Val Val Leu Ala Pro
            405                 410                 415

Thr Glu Leu Leu Asp Gly Gly Val His Ala Leu Thr Cys Ile Gly Pro
                420                 425                 430

Ala Ser Lys Glu Thr Ser Arg His Tyr Phe Arg Glu Pro Leu Val Glu
            435                 440                 445

Glu Ala Met Ala Asp Glu Asp Ile Asp Leu Val Gly Ile Ala Leu Val
450                 455                 460

Gly Ser Pro Gln Glu Asn Val Gln Lys Phe Tyr Val Ser Lys Arg Leu
465                 470                 475                 480

Gly Met Met Val Glu Ala Met Asn Leu Asp Gly Ala Ile Val Thr Thr
                485                 490                 495

Glu Gly Phe Gly Asn Asn His Ile Asp Phe Ala Ser His Ile Glu Gln
            500                 505                 510

Ile Gly Glu Arg Gly Val Asp Val Val Gly Met Thr Tyr Ala Ala Val
        515                 520                 525

Gln Gly Gln Leu Val Val Gly Asn Lys Tyr Met Asp Ala Met Val Asp
530                 535                 540

Asn Asn Lys Ser Arg Gln Gly Ile Glu Asn Ile Leu Glu Asn Asn
545                 550                 555                 560

Thr Leu Ser Arg Glu Asp Ala Ile Arg Ala Leu Ala Met Leu Glu Thr
                565                 570                 575

Lys Met Ala Gly Gly Ser Ile Lys Lys Pro Glu Arg Gln Trp Asn Pro
            580                 585                 590

Asn Val Lys Gln Asn Asn Ile Glu Ile Ile Glu Lys Glu Thr Gly Lys
        595                 600                 605

Lys Ile Asp Leu Val Glu Asn Glu Gln Ser Leu Pro Met Ser Lys Lys
610                 615                 620

Arg Arg Glu Ile Tyr Glu Lys Asp Ala Gln
625                 630
```

<210> SEQ ID NO 20
<211> LENGTH: 1905
<212> TYPE: DNA
<213> ORGANISM: Lactobacillus salivarius
<220> FEATURE:
<221> NAME/KEY: gene
<222> LOCATION: (1)..(1905)
<223> OTHER INFORMATION: PrdA(LsPrdA)

<400> SEQUENCE: 20
atgtcaattt cagttgaaca agctaaagaa catgctaagg atccagcagt tctttgctgt    60
agaagagagg caggaaaagt tctggaagct gccgattttg aagacccaac tttgtttgat   120

|  |  |
|---|---|
| gactatgtta gttcaggact tttagaaata cctgaagata cgttaactat tgaacaagca | 180 |
| ttgggtgcaa cattaaatac tactacggat gcattaaatc ctttagttcc aggtattgta | 240 |
| gataatattc agggaaatga agaagcatct gaaagtgata aggacgaaaa tgttgaagaa | 300 |
| gaaacaccag ttgtagcaga agctaacaat gaagtagtaa attcaacatc atcaaatggt | 360 |
| acattccatt taagaatcgc taaaggtgaa ggtattgatt tagaaatacc tttggatgta | 420 |
| ttaaaaaaaa acacagctaa ctcagctgta gatgtcccca aggcggaaac aagtgctgat | 480 |
| gtaactaata aggatgttgc agaagatgaa gaatcagcag aagatgctaa agttgttcgt | 540 |
| actctaacta aaaaatactt caaagtagat gaagttaaat ttggagacac aacaaagttt | 600 |
| gatggaacaa cactttactt acgtaatcct aaagaacttt gcaagaagc tgttgatact | 660 |
| gaagcaatcg ttaagggtat ggaaatcgaa attatcacac ctgatgatta ttccaactat | 720 |
| agtaacacta ttatggatgt tcaaccaatc gctacaaaag aaggagatag tgatttgggt | 780 |
| gtaggcgtta caaagttgt ggatggtgct gtagtagtac tcacaggtac tgatgaaaat | 840 |
| ggtgtccaag ttggtgaatt tggttcttca gaaggtccat tgaatgaaaa tattatgtgg | 900 |
| aatcgtcctg gtgcagttga taaaggcgaa atcatgatta agattgatgt tgttatcgaa | 960 |
| gctggaacta accgtgaacg taaaggacct ttaggagcac atttagcagc agactacatt | 1020 |
| acacaagaaa ttagagaagc actaaaagat gttgatgata gttcagcagt tagaactgaa | 1080 |
| gaatttgttc aaaacgtca tcctaagcaa aagagagtat taattgtaaa agaaatcatg | 1140 |
| ggtcaaggtg caatgcacga taatttaatt atgcctgtgg aaccagttgg tactcttggt | 1200 |
| gcaaagccaa atgttgattt aggtaacttg ccagttgtat tagctccaac ggaattatta | 1260 |
| gatggtggtg tacatgcttt aacatgtatt ggacctgctt ctaaggaaac atccagacat | 1320 |
| tacttcagag aacctttggt agaagaagca atggctgatg aagatattga tttagttgg | 1380 |
| attgcattag tcggttcacc tcaagaaaat gttcaaaaat tctatgtttc taagagatta | 1440 |
| ggtatgatgg tagaagctat gaattagat ggtgctattg ttacaacaga aggatttggt | 1500 |
| aataaccata tcgactttgc ttctcacatc gaacaaattg gtgaaagagg agtagatgtt | 1560 |
| gttggaatga catatgctgc tgtccaagga caattagttg ttggtaacaa gtatatggat | 1620 |
| gcaatggtgg ataacaacaa atcccgtcaa ggtattgaaa acgaaattct tgaaaacaat | 1680 |
| actctatcac gtgaagatgc tatcagagct ttagcaatgt tggaaacaaa gatggctggt | 1740 |
| ggatcaatta agaaacctga acgtcaatgg aatccaaatg ttaagcaaaa taatatcgaa | 1800 |
| attattgaaa agaaaccgg taagaagatt gacttagttg agaatgaaca atctctacca | 1860 |
| atgagtaaga agcgtcgtga aatttacgaa aaggatgctc aatag | 1905 |

<210> SEQ ID NO 21
<211> LENGTH: 240
<212> TYPE: PRT
<213> ORGANISM: Lactobacillus salivarius
<220> FEATURE:
<221> NAME/KEY: PEPTIDE
<222> LOCATION: (1)..(240)
<223> OTHER INFORMATION: PrdB(LsPrdB)

<400> SEQUENCE: 21

Met Ser Leu Lys Lys Tyr Asp Gly Leu Gln Ser Glu Ile Phe Val Pro
1               5                   10                  15

Ile Thr Pro Thr Pro Val Trp Ala Pro Val Lys Lys Lys Leu Lys Asp
            20                  25                  30

Met Thr Val Ala Ile Val Thr Ala Ala Gly Val His Leu Lys Ser Asp

```
                35                  40                  45
Lys Pro Phe Asn Leu Ala Gly Asp Thr Ser Tyr Arg Val Val Pro Ser
 50                  55                  60

Thr Ala Thr Asp Asp Glu Leu Met Val Ser His Gly Gly Tyr Asp Asn
 65                  70                  75                  80

Thr Asp Val Asn Arg Asp Ile Asn Cys Met Phe Pro Ile Asp Arg Leu
                 85                  90                  95

Arg Glu Leu Ala Glu Lys Gly Phe Ile Lys Asn Ile Ala Pro Asn Met
            100                 105                 110

Tyr Thr Cys Met Gly Gly Gly Asp Val Lys Val Phe Thr Glu Glu
        115                 120                 125

Thr Gly Pro Glu Ile Ala Gln Lys Leu Leu Asp Glu His Val Asp Ala
    130                 135                 140

Val Val Met Thr Ala Gly Gly Thr Cys His Arg Thr Ala Val Ile Val
145                 150                 155                 160

Gln Arg Ala Ile Glu Ser Val Gly Ile Pro Thr Ile Ile Ala Ala
                165                 170                 175

Leu Pro Pro Val Val Arg Gln Gln Gly Ser Pro Arg Ala Val Ala Pro
            180                 185                 190

Arg Val Pro Met Gly Ala Asn Ala Gly Glu Pro His Asn Val Glu Met
        195                 200                 205

Gln Thr Gly Ile Leu Lys Asp Thr Leu Glu Gln Leu Glu Lys Leu Asp
    210                 215                 220

Ser Pro Gly Lys Ile Val Pro Leu Pro Tyr Glu Tyr Ile Ala Asn Ile
225                 230                 235                 240

<210> SEQ ID NO 22
<211> LENGTH: 726
<212> TYPE: DNA
<213> ORGANISM: Lactobacillus salivarius
<220> FEATURE:
<221> NAME/KEY: gene
<222> LOCATION: (1)..(726)
<223> OTHER INFORMATION: PrdB(LsPrdB)

<400> SEQUENCE: 22
atgagtctta agaaatatga tggactacaa tccgaaatat ttgtacctat tactcctacg      60
ccagtgtggg ctccagttaa aagaagcta aaagatatga ctgtagcaat gtaactgct      120 gctggtgtac atttgaaatc agataaacca tttaatttag ctggtgatac ttcatataga      180
gtagtacctt caactgcaac tgatgatgaa ttgatggtat cacatggtgg ttatgataac      240
actgatgtta acagagatat taactgtatg ttcccaattg atagattaag agaacttgca      300
gagaaaggat ttattaagaa tattgcgcca aacatgtata catgtatggg tggtggtgga      360
gacgttaaag tctttactga agaaactggt ccagaaattg cccaaaaatt attggatgaa      420
catgtagatg ctgtcgtaat gactgctggt tgaggtacct gtcatagaac tgccgtgatc      480
gtgcagagag ctattgaatc agttggtatc ccaacaatta ttattgcagc cttacctcca      540
gtagtacgtc aacaaggatc tcctagagct gttgctcctc gagttcctat gggggctaat      600
gccggagaac cacacaacgt cgaaatgcaa acaggtattt tgaaagatac gttagagcaa      660
ttagaaaaat tagattcccc aggtaagatt gtgccactac catatgaata tagcaaat      720 atatag                                                              726

<210> SEQ ID NO 23
<211> LENGTH: 105
```

```
<212> TYPE: PRT
<213> ORGANISM: Lactobacillus salivarius
<220> FEATURE:
<221> NAME/KEY: PEPTIDE
<222> LOCATION: (1)..(105)
<223> OTHER INFORMATION: PrdH(LsPrdH)

<400> SEQUENCE: 23

Met Glu Glu Gln Ser Thr Gly Phe Asp Lys Leu Lys Tyr Ala Ser Thr
1               5                   10                  15

Glu Arg Val Trp Glu Gly Ile Ile Glu Leu Thr Asp Ala Ser Val
            20                  25                  30

Ile Ile Asp Leu Lys Gly Arg Leu Gly Arg Leu Glu Ile Pro Asn Arg
        35                  40                  45

Met Ile Ile Ser Asp Tyr Glu Leu Lys Val Gly Gln Glu Val Ala Phe
    50                  55                  60

Leu Met Ser Tyr Pro Glu Val Leu Asp Ser Glu Pro Asn Gln Lys Tyr
65              70                  75                  80

Leu Gly Ala Leu Asn Ala Tyr His Lys Lys Met Lys Glu Ile Lys Glu
                85                  90                  95

Lys Gln Arg Arg Asp Lys Asn Glu Ser
            100                 105

<210> SEQ ID NO 24
<211> LENGTH: 318
<212> TYPE: DNA
<213> ORGANISM: Lactobacillus salivarius
<220> FEATURE:
<221> NAME/KEY: gene
<222> LOCATION: (1)..(318)
<223> OTHER INFORMATION: PrdH(LsPrdH)

<400> SEQUENCE: 24
atggaagaac aaagtacagg atttgacaag ttgaaatatg cctcaactga aagagtatgg      60
gagggtataa aatagaatt gacagatgcg agtgtcataa ttgatcttaa aggacgtcta     120
ggtagactag aaattcctaa tagaatgatt attagtgact atgagttgaa agtcggtcag     180
gaagtagcat tcttaatgtc atatcccgaa gttttggata gtgaacctaa tcaaaaatat     240
ttaggagcac taaatgcata ccataaaaaa atgaaagaaa taaagaaaaa gcaaaggaga     300
gataaaaatg agtcttaa                                                  318

<210> SEQ ID NO 25
<211> LENGTH: 40
<212> TYPE: DNA
<213> ORGANISM: Artificial Sequence
<220> FEATURE:
<223> OTHER INFORMATION: PrdA(C421A)-F

<400> SEQUENCE: 25
ggtatccatg cattaactgc cataggacct gcatcaaaag                            40

<210> SEQ ID NO 26
<211> LENGTH: 40
<212> TYPE: DNA
<213> ORGANISM: Artificial Sequence
<220> FEATURE:
<223> OTHER INFORMATION: PrdA(C421A)-R

<400> SEQUENCE: 26
cttttgatgc aggtcctatg gcagttaatg catggatacc                            40
```

US 11,708,564 B2

MICROORGANISM EXPRESSING ACTIVE D-PROLINE REDUCTASE AND METHOD OF PRODUCING ACTIVE D-PROLINE REDUCTASE

SEQUENCE LISTING SUBMISSION VIA EFS-WEB

A computer readable text file, entitled "SequenceListing.txt," created on or about Oct. 30, 2020 with a file size of about 44 kb contains the sequence listing for this application and is hereby incorporated by reference in its entirety.

TECHNICAL FIELD

The present disclosure relates to a microorganism expressing D-proline reductase, in which activities of PrdA protein, PrdB protein, and PrdH protein are enhanced; and a method of producing the corresponding active D-proline reductase. On this basis, the present disclosure also relates to a method of reducing D-proline and a D-proline analog; and PrdH protein having activity to convert inactive D-proline reductase into active D-proline reductase while being co-expressed with the PrdA protein and the PrdB protein.

BACKGROUND ART

Due to the trends of development of eco-friendly products as well as unstable oil supply and oil depletion crisis, research and development have been conducted on biomass-derived products such as bioplastics, bioenergy, etc. In particular, many studies are being made to apply various biomass-derived monomers to nylon. For example, development of nylon 4,6 through application of biomass-derived putrescine, and nylon 5,6 as an alternative to hexamethylene diamine (HMDA) of nylon 6,6 through application of biomass-derived cadaverine are being studied. Development of nylon 4 products by using 4-aminobutyric acid (or gamma-aminobutyric acid (GABA)) as a monomer which may be produced from glutamic acid as a raw material by glutamate decarboxylase is also in progress.

5-Aminovaleric acid which is a monomer of nylon 5 is known to be converted from proline by D-proline reductase. However, activation of the D-proline reductase requires precise self-cleavage of PrdA protein and introduction of a pyruvoyl group at the same time. However, this is considered as a technical limitation, and thus there is an increasing demand for a method capable of preparing active D-proline reductase.

DISCLOSURE

Technical Problem

The present inventors have continued to study a recombinant expression system and a microorganism strain which may produce D-proline reductase in an active form, and also to study its applicability to various D-proline analog substrates. As a result, they for the first time identified PrdH protein which converts inactive D-proline reductase into active D-proline reductase while being co-expressed with the PrdA protein and the PrdB protein. Further, they successfully demonstrated a microorganism expressing the active D-proline reductase and activity of the D-proline reductase produced therefrom.

Technical Solution

An object of the present disclosure is to provide a microorganism expressing active D-proline reductase, in which activities of PrdA protein, PrdB protein, and PrdH protein are enhanced.

Another object of the present disclosure is to provide a method of producing active D-proline reductase, the method including the steps of culturing the microorganism in a medium, and recovering the active D-proline reductase from the microorganism or the medium.

Still another object of the present disclosure is to provide a method of producing one or more selected from the group consisting of aminovaleric acid (5-aminovaleric acid, 5-AVA), γ-aminobutyric acid (GABA) and 5-amino-4-hydroxypentanoic acid using the microorganism or the active D-proline reductase produced by the microorganism.

Still another object of the present disclosure is to provide PrdH protein converting inactive D-proline reductase into active D-proline reductase while being co-expressed with PrdA protein and PrdB protein.

Still another object of the present disclosure is to provide a method of producing the microorganism expressing the active D-proline reductase, the method including the steps of transforming a host cell with an expression cassette including prdA gene or prdA and prdH genes and transforming the host cell with an expression cassette including prdB gene or prdB and prdH genes.

Advantageous Effects

In the present disclosure, a polypeptide capable of converting inactive D-proline reductase into active D-proline reductase has been newly suggested, and activity of the active D-proline reductase is enhanced when expressed by interacting with a complex of PrdA and PrdB constituting the existing D-proline reductase or when expressed together with Prd operon, thereby providing a novel active form of D-proline reductase and a method of converting D-proline or analogs thereof.

DESCRIPTION OF DRAWINGS

FIG. 1 is a schematic diagram illustrating a method of producing active D-proline reductase;

FIG. 2 shows results of SDS-PAGE analysis according to expression conditions of PrdA protein;

FIG. 3 shows results of SDS-PAGE analysis of PrdA protein expression with or without shaking;

FIG. 4 shows results of Western blot analysis according to PrdB protein expression;

FIG. 5 shows results of Western blot analysis for self-cleavage of PrdA protein by PrdH protein;

FIG. 6 shows results of TLC analysis for activities of the recombinant D-proline reductase and PrdDEE$_2$ protein;

FIG. 7 shows results of Western blot analysis for universal application of PrdH protein;

FIG. 8 shows results of TLC analysis for the effect of PrdC protein on the activity of D-proline reductase;

FIG. 9 shows results of TLC analysis for the effect of PrdG protein on the activity of D-proline reductase (A) and characterization of PrdG protein (B);

FIG. 10 shows results of TLC analysis for production of 5-aminovaleric acid from a sugar source by co-expressing the recombinant active D-proline reductase and additional protein; and FIG. 11 shows results of TLC analysis for D-proline analog-converting ability of the active D-proline reductase.

BEST MODE

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

To achieve the objects of the present disclosure, one aspect of the present disclosure provides a microorganism expressing active D-proline reductase, in which activities of PrdA protein, PrdB protein, and PrdH protein are enhanced.

As used herein, the term "D-proline reductase" refers to a protein complex consisting of PrdA protein and PrdB protein. Its major function is known to be involved in a conversion process of reducing D-Proline to 5-aminovaleric acid (5-AVA). This reaction is known to correspond to the last step of Stickland reaction which is utilized for energy source (ATP) supply of anaerobic strains (Bouillaut et al., J. Bacteriol., 2013, 195(4), 844-854).

The Stickland reaction, also called Stickland fermentation, refers to a reaction that involves the coupled oxidation and reduction of amino acids to organic acids. In detail, the electron donor amino acid is oxidized to a volatile carboxylic acid one carbon atom shorter than the original amino acid. For example, alanine with a three-carbon chain is converted to acetate with two carbons. Amino acids may act as Stickland acceptor and Stickland donor.

Representative strains having the Stickland reaction may include *Peptoclostridium difficile* 630, *Clostridium difficile* 630, *Peptoclostridium sticklandii*, *Clostridium sticklandii*, or *Eubacterium acidaminophilum*. Some of *Lactobacillus* strains, such as *Lactobacillus salivarius*, are known to be also included. Therefore, these strains may be used to produce the microorganism expressing the active D-proline reductase of the present disclosure, the PrdH protein having activity to convert the inactive D-proline reductase into the active D-proline reductase, and the active D-proline reductase.

A major function of D-proline reductase is known to be involved in the conversion process of D-proline into 5-aminovaleric acid (5-AVA). However, no clear reaction mechanism for D-proline reductase has been known until now, but the following reaction mechanism has been suggested. First, among constitutive proteins of D-proline reductase consisting of a complex of alpha-PrdA, beta-PrdA, and PrdB proteins, the alpha-PrdA protein has a pyruvoyl group at the amino terminus, which interacts with an amine group of D-proline as a substrate, and as a result, the activation energy of the substrate is lowered. In the next step, a C—N bond between alpha carbon and the amine group of D-proline is broken by selenocysteine located at PrdB protein, and as a result, a conversion reaction of D-proline into 5-aminovaleric acid occurs (Kabisch et al., J. Biol. Chem., 1999, 274(13), 8445-8454). As used herein, the term "active D-proline reductase" refers to a protein complex consisting of alpha-PrdA, beta-PrdA, and PrdB proteins, in which, of the PrdA protein and the PrdB protein constituting D-proline reductase, PrdA protein is separated into alpha-PrdA and beta-PrdA due to precise self-cleavage by PrdH which is an auxiliary protein of the present disclosure, and a pyruvoyl group binds to the amino terminus of alpha-PrdA. The active D-proline reductase as described above refers to an active form of the enzyme, which is able to reduce D-proline or D-proline analog substrates via binding of the pyruvoyl group of alpha-PrdA to the substrate. For example, the active D-proline reductase is able to convert the substrate D-proline into 5-aminovaleric acid (5-aminovalerate).

As used herein, the term "D-proline" is an optical isomer of L-proline which is an α-amino acid. In particular, L-proline, which is a non-essential amino acid, may be synthesized from L-glutamate and converted into D-proline by racemase.

As used herein, the term "PrdA protein" refers to a component constituting the protein complex of D-proline reductase, and the PrdA protein is separated into alpha-PrdA protein (carboxyl terminal fragment) and beta-PrdA protein (amino terminal fragment) through a self-cleavage process. A general self-cleavage process occurs through simple cleavage of peptide bonds, but the self-cleavage process of PrdA protein is characterized in that the cleavage process of peptide bonds and introduction of a pyruvoyl group into the amino terminus of the alpha-PrdA protein occur at the same time. When PrdA protein exists independently, non-specific cleavage/degradation processes are involved due to imperfection of the protein itself, and there is a problem in that PrdA protein is not completely separated into alpha-PrdA protein and beta-PrdA protein.

The pyruvoyl group is known as an essential residue for the activity of D-proline reductase, because it plays a role in lowering the activation energy of the substrate (Kabisch et al., J. Biol. Chem., 1999, 274(13), 8445-8454). However, in the protein cleavage mechanism through a general hydrolysis reaction, the pyruvoyl group is not introduced, and thus various studies have been conducted to solve this problem. In order to prevent non-specific protein degradation caused by structural instability of PrdA protein (pro-PrdA protein) itself, a study has been conducted to induce an artificial cleavage process by adding a reducing agent such as $NaBH_4$, etc. to the PrdA protein fragment from which the amino terminus is removed. As a result, the desired site-specific cleavage was observed, but the introduction of the pyruvoyl group was not obtained (Bednarski et al., Eur. J. Biochem., 2001, 268, 3538-3544).

A sequence of the PrdA protein may be available from GenBank of NCBI, which is a public database, and any sequence may be used without limitation, as long as it encodes the PrdA protein of a strain having the Stickland reaction. A representative example thereof may include PrdA protein derived from *Peptoclostridium difficile* 630 (*Clostridium difficile* 630) or *Lactobacillus salivarius*, but is not limited thereto. For example, it may be an amino acid sequence of SEQ ID NO: 3 or an amino acid sequence encoded by a sequence of SEQ ID NO: 19, but is not limited thereto. Specifically, the PrdA protein of the present disclosure may include a polypeptide having at least 40%, 50%, 60%, 70%, 80%, 85%, 90%, 95%, 96%, 97%, 98%, or 99% homology or identity to SEQ ID NO: 3 and SEQ ID NO: 19. Further, it is apparent that PrdA protein having an amino acid sequence, part of which is deleted, modified, substituted, conservatively substituted, or added, may also be within the scope of the present disclosure, as long as the amino acid sequence has the above homology or identity and exhibits efficacy corresponding to the above protein.

As used herein, the term "PrdB protein" refers to a component constituting the protein complex of D-proline reductase, and the PrdB protein is a seleno protein including selenocysteine (Sec) which is a non-natural amino acid. Selenocysteine is a non-natural amino acid called the $21^{st}$ amino acid, and is characterized by not being introduced into a protein through normal protein synthesis mechanisms (Itoh et al., Science, 340(6128), 2013, 75-78.). In particular, since its introduction is performed using UGA codon, i.e., stop codon among 64 codons, there is a phenomenon in which protein synthesis stops at the stop codon without a selenocysteine insertion system. In addition, in order not to recognize the selenocysteine insertion codon as a general stop codon, a secondary structure of a sequence/structure specific mRNA called SECIS (SElenoCysteine Incorporation Sequence) must be located downstream of UGA codon, and for incorporation into a protein, a Sel system (SelABCD) is required (Su et al., Nucleic Acids Res., 2005, 33(8), 2486-2492).

A sequence of the PrdB protein may be available from GenBank of NCBI, which is a public database, and any sequence may be used without limitation, as long as it encodes the PrdB protein of a strain having the Stickland reaction. A representative example thereof may include PrdB protein derived from *Peptoclostridium difficile* 630 (*Clostridium difficile* 630) or *Lactobacillus salivarius*, but is not limited thereto. For example, it may be an amino acid sequence of SEQ ID NO: 5 or an amino acid sequence encoded by a polypeptide sequence of SEQ ID NO: 21, but is not limited thereto. Specifically, the PrdB protein of the present disclosure may include a polypeptide having at least 40%, 50%, 60%, 70%, 80%, 85%, 90%, 95%, 96%, 97%, 98%, or 99% homology or identity to SEQ ID NO: 5 and SEQ ID NO: 21. Further, it is apparent that PrdB protein having an amino acid sequence, part of which is deleted, modified, substituted, conservatively substituted, or added, may also be within the scope of the present disclosure, as long as the amino acid sequence has the above homology or identity and exhibits efficacy corresponding to the above protein.

As used herein, the term "PrdH protein" refers to a novel protein encoded by using gene ORF, which is present between genes encoding PrdA protein and PrdB protein constituting the D-proline reductase. In the present disclosure, it is called PrdH. Further, according to species or characteristics of strains having D-proline reductase activity, the PrdH protein may be partially overlapped with PrdA or PrdB, and the stop codon of PrdH may be located after the start codon of PrdB, but is not limited thereto.

The PrdH protein may be co-expressed with PrdA protein and PrdB protein to induce precise self-cleavage of PrdA protein and introduction of the pyruvoyl group, thereby allowing construction of the active D-proline reductase. Specifically, any sequence may be used without limitation, as long as it encodes the PrdH protein of a strain having the Stickland reaction. In other words, any sequence may be used without limitation, as long as it includes gene ORF present between genes encoding PrdA protein and PrdB protein of a strain having the Stickland reaction. A representative example thereof may include PrdH protein derived from *Peptoclostridium difficile* 630 (*Clostridium difficile* 630) or *Lactobacillus salivarius*, but is not limited thereto. PrdH protein derived from *Peptoclostridium difficile* 630 and PrdH protein derived from *Lactobacillus salivarius* have 40% homology or identity to each other, and they are in common the gene ORF present between genes encoding PrdA protein and PrdB protein derived from each of the two microorganisms. More specifically, the PrdH protein may be, for example, an amino acid sequence encoded by a polypeptide sequence composed of an amino acid sequence of SEQ ID NO: 1 or SEQ ID NO: 23, but is not limited thereto.

Further, the PrdH protein of the present disclosure may include a polypeptide having at least 40%, 50%, 60%, 70%, 80%, 90%, 95%, 96%, 97%, 98%, or 99% homology or identity to SEQ ID NO: 1 or SEQ ID NO: 23. Further, it is apparent that PrdH protein having an amino acid sequence, part of which is deleted, modified, substituted, conservatively substituted, or added, may also be within the scope of the present disclosure, as long as the amino acid sequence has the above homology or identity and exhibits efficacy corresponding to the above protein.

As used herein, the term 'homology' or 'identity' means the degree of relevance between two given amino acid sequences or nucleotide sequences, and may be expressed as a percentage. The terms 'homology' and 'identity' may be often used interchangeably.

The sequence homology or identity of the conserved polynucleotide or polypeptide may be determined by standard alignment algorithms, and may be used with default gap penalties established by the used program. Substantially, homologous or identical sequences may hybridize under moderately or highly stringent conditions such that the full length of the sequence or at least about 50%, 60%, 70%, 80%, or 90% or more of the full-length may hybridize. Also, contemplated are polynucleotides that contain degenerate codons in place of codons in the hybridization.

Whether or not any two polynucleotide or polypeptide sequences have homology, similarity, or identity may be determined using known computer algorithms such as the "FASTA" program, using, for example, the default parameters as in Pearson et al (1988)[Proc. Natl. Acad. Sci. USA 85]: 2444, or determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, BLAST of the National Center for Biotechnology Information database, or ClustalW may be used to determine homology, similarity, or identity.

Homology, similarity, or identity of polynucleotides or polypeptides may be determined, for example, by comparing sequence information using a GAP computer program such as Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids), which are similar, divided by the total number of symbols in the shorter of the two sequences. Default parameters for the GAP program may include: (1) a binary comparison matrix (containing a value of 1 for identities and 0 for non-identities) and the weighted comparison matrix of Gribskov et al(1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or gap open penalty of 10, gap extension penalty of 0.5); and (3) no penalty for end gaps. Therefore, as used herein, the term "homology" or "identity" represents relevance between sequences.

Further, even though 'a protein having an amino acid sequence of a particular SEQ ID NO' is described herein, it is apparent that a protein having an amino acid sequence, part of which is deleted, modified, substituted, conservatively substituted, or added, may be used in the present disclosure, as long as it has activity identical or corresponding to that of the polypeptide composed of the amino acid sequence of the corresponding SEQ ID NO. Specifically, addition of a sequence that does not alter the function of the protein before and after the amino acid sequence of the corresponding SEQ ID NO., naturally occurring mutations, conservative substitutions, or synonymous mutations thereof are not excluded. It is apparent that even though the polypeptide has such a sequence addition or mutation, it falls within the scope of the present disclosure.

As used herein, the term "conservative substitution" means substitution of one amino acid with another amino acid having similar structural and/or chemical properties in an amino acid sequence. The variant may have, for example, one or more conservative substitutions while retaining one or more biological activities. Such amino acid substitutions may be generally made on the basis of similarity in polarity, charge, solubility, hydrophobicity, hydrophilicity, and/or the amphipathic nature of residues. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan. Commonly, conservative substitution has little or no effect on the activity of the resulting polypeptide. The polynucleotide encoding the PrdH protein having the amino acid sequence composed of SEQ ID NO: 1 or SEQ ID NO: 23 also falls within the scope of the present disclosure. For example, the polynucleotide may be a polynucleotide composed of a nucleotide sequence of SEQ ID NO: 2 or SEQ ID NO: 24. In the polynucleotide, various modifications may be made in the coding region provided that they do not change the amino acid sequence of the protein, due to codon degeneracy or in consideration of the codons preferred by the organism in which the protein is to be expressed.

It is apparent that, due to codon degeneracy, a polynucleotide which may be translated into the protein composed of the amino acid sequence of SEQ ID NO: 1 or SEQ ID NO: 23 or the protein having homology or identity thereto may also be included. Further, a probe which may be produced from a known nucleotide sequence, for example, a sequence which hybridizes with a complementary sequence to all or a part of the nucleotide sequence under stringent conditions to encode a protein having the activity of the protein composed of the amino acid sequence of SEQ ID NO: 1 may also be included without limitation. The term "stringent conditions" mean conditions under which specific hybridization between polynucleotides is allowed. Such conditions are described in detail in a literature (e.g., J. Sambrook et al., supra). For example, the stringent conditions may include, for example, conditions under which genes having high homology or identity, 40% or higher, 85% or higher, specifically 90% or higher, more specifically 95% or higher, much more specifically 97% or higher, particularly specifically 99% or higher homology or identity are hybridized with each other and genes having homology or identity lower than the above homology or identity are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS.

Although a mismatch between nucleotides may occur due to the stringency of hybridization, it is required that the two nucleic acids have a complementary sequence. The term "complementary" is used to describe the relationship between nucleotide bases which may hybridize with each other. For example, with respect to DNA, adenosine is complementary to thymine and cytosine is complementary to guanine. Accordingly, the present disclosure may include not only the substantially similar nucleic acid sequences but also isolated nucleic acid fragments which are complementary to the entire sequence.

Specifically, the polynucleotide having homology or identity may be detected using hybridization conditions including the hybridization step at a Tm value of 55° C. and the conditions described above. Additionally, the Tm value may be 60° C., 63° C., or 65° C., but is not limited thereto, and may be appropriately controlled by one of ordinary skill in the art according to the purposes.

Appropriate stringency for the hybridization of polynucleotides depends on the length and degree of complementarity of the polynucleotides, and the variables are well-known in the art (see Sambrook et al., supra, 9.50-9.51, 11.7-11.8).

As used herein, the term "enhancement of the activity" means introduction of the activity of the enzyme protein, or improvement thereof, as compared with the intrinsic activity of the microorganism or the activity before modification. The "introduction" of the activity means that the activity of a specific protein that is not originally possessed by a microorganism appears naturally or artificially. The "intrinsic activity" refers to the activity of a specific protein originally possessed by a parent strain before transformation, when the trait of the microorganism is changed due to genetic variation caused by natural or artificial factors.

For example, the enhancement of the activity may include all of introduction of a foreign D-proline reductase into a host cell or enhancement by the introduction, or enhancement of the intrinsic D-proline reductase activity.

Specifically, in the present disclosure, the enhancement of activity may be performed by:

1) increasing the copy number of the polynucleotides encoding the enzymes, 2) modifying the expression control sequence for increasing the expression of the polynucleotides, 3) modifying the polynucleotide sequence on the chromosome for enhancing the activities of the enzymes, or 4) modifying for the enhancement by a combination thereof, but is not limited thereto.

1) The increase of the copy number of the polynucleotide may be, but is not particularly limited to, performed in a form in which the polynucleotide is operably linked to a vector, or by inserting the polynucleotide into the chromosome of a host cell. Further, the increase of the copy number may be carried out by introducing a foreign polynucleotide exhibiting the enzyme activity or a codon-optimized variant polynucleotide of the polynucleotide into a host cell. Any foreign polynucleotide sequence may be used without limitation in the origin or sequence thereof, as long as it exhibits the activity identical/similar to that of the above enzyme. The introduction may be carried out by a known transformation method which is appropriately selected by those skilled in the art, and the enzyme may be produced by expression of the introduced polynucleotide in the host cell, and as a result, its activity may be increased.

Next, 2) the modification of the expression control sequence for increasing the expression of the polynucleotide may be, but is not particularly limited to, performed by inducing a modification on the sequence through deletion, insertion, non-conservative or conservative substitution of the nucleotide sequence, or a combination thereof to further enhance the activity of the expression control sequence, or by replacing the polynucleotide sequence with a nucleotide sequence having a stronger activity. The expression control sequence includes, but is not particularly limited to, a promoter, an operator sequence, a sequence encoding a ribosome-binding site, and a sequence regulating the termination of transcription and translation. Specifically, a strong exogenous promoter, instead of the original promoter, may be connected to the upstream region of the expression unit of the polynucleotide. Examples of the strong promoter may include CJ7 promoter, lysCP1 promoter, EF-Tu promoter, groEL promoter, aceA or aceB promoter, etc. The promoter and the polynucleotide are operably linked to each other to improve an expression rate of the polynucleotide encoding the enzyme, but is not limited thereto.

Furthermore, 3) the modification of the polynucleotide sequence on the chromosome may be, but is not particularly limited to, performed by inducing a modification on the expression control sequence through deletion, insertion, non-conservative or conservative substitution of the polynucleotide sequence, or a combination thereof to further enhance the activity of the polynucleotide sequence, or by replacing the polynucleotide sequence with a polynucleotide sequence which is improved to have a stronger activity.

Lastly, 4) the method of modifying for the enhancement by a combination of 1) to 3) may be performed by applying one or more of the methods of increasing the copy number of the polynucleotide encoding the protein, modifying the expression control sequence for increasing the expression of the polynucleotide, modifying the polynucleotide sequence on the chromosome, and introducing a foreign polynucleotide exhibiting the activity of the protein or a variant polynucleotide in which the codons thereof are codon-optimized.

As used herein, the term "vector" is a DNA construct that includes a nucleotide sequence of a polynucleotide encoding a desired protein operably linked to an appropriate regulatory sequence to enable expression of the desired protein in an appropriate host cell. The regulatory sequence may include a promoter capable of initiating transcription, any operator sequence for the regulation of such transcription, a sequence encoding an appropriate mRNA ribosome-binding domain, and a sequence regulating termination of transcription and translation. After the vector is transformed into the appropriate host cell, it may replicate or function independently of the host genome, and may be integrated into the genome itself.

The vector used in the present disclosure is not particularly limited, as long as it is able to replicate in the host cell, and any vector known in the art may be used. Examples of commonly used vectors may include a natural or recombinant plasmid, cosmid, virus, and bacteriophage. For instance, pWE15, M13, MBL3, MBL4, IXII, ASHII, APII, t10, t11, Charon4A, Charon21A, etc. may be used as a phage vector or cosmid vector. As a plasmid vector, pBR type, pUC type, pBluescriptII type, pGEM type, pTZ type, pCL type, pET type, etc. may be used. Specifically, pDZ, pACYC177, pACYC184, pCL, pECCG117, pUC19, pBR322, pMW118, pCC1BAC vector, etc. may be used, but is not limited thereto.

The vector applicable in the present disclosure is not particularly limited, and a known expression vector may be used. Further, the polynucleotide encoding the desired protein may be inserted into the chromosome using a vector for intracellular chromosomal insertion. The chromosomal insertion of the polynucleotide may be performed by any method known in the art, for example, homologous recombination, but is not limited thereto. A selection marker to confirm the chromosomal insertion may be further included. The selection marker is to select cells transformed with the vector, that is, to confirm insertion of the desired polynucleotide, and the selection marker may include markers providing selectable phenotypes, such as drug resistance, auxotrophy, resistance to cytotoxic agents, or expression of surface proteins. Since only cells expressing the selection marker are able to survive or to show different phenotypes under the environment treated with a selective agent, the transformed cells may be selected.

As used herein, the term "transformation" means introduction of a vector including a polynucleotide encoding a desired protein into a host cell in such a way that the protein encoded by the polynucleotide is expressed in the host cell. As long as the transformed polynucleotide is expressed in the host cell, it may be integrated into and placed in the chromosome of the host cell, or it may exist extrachromosomally, or irrespective thereof. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette includes a promoter operably linked to the polynucleotide, transcriptional termination signals, ribosome binding sites, and translation termination signals. Further, various factors to help efficient production of a target protein may be included inside or outside the expression cassette. The expression cassette may be in the form of a self-replicable expression vector. Also, the polynucleotide as it is may be introduced into the host cell and operably linked to sequences required for expression in the host cell, but is not limited thereto. A method of performing the transformation may include any method of introducing nucleic acids into a cell, and the transformation may be performed by selecting an appropriate standard technique as known in the art according to the host cell.

For example, the method may include electroporation, calcium phosphate ($CaPO_4$) precipitation, calcium chloride ($CaCl_2$) precipitation, microinjection, a polyethylene glycol (PEG) method, a DEAE-dextran method, a cationic liposome method, and a lithium acetate-DMSO method, etc., but is not limited thereto.

As used herein, the term "operably linked" means a functional linkage between the polynucleotide sequence encoding the desired protein of the present disclosure and a promoter sequence which initiates and mediates transcription of the polynucleotide. The operable linkage may be prepared using a genetic recombinant technology known in the art, and site-specific DNA cleavage and linkage may be prepared using restriction and ligation enzymes, etc., in the art, but is not limited thereto.

Further, a specific embodiment of the present disclosure provides a microorganism expressing the active D-proline reductase, in which activities of one or more proteins selected from the group consisting of PrdD, PrdE, and $PrdE_2$ are enhanced, in addition to the microorganism expressing the active D-proline reductase, in which the activities of PrdA protein, PrdB protein, and PrdH protein are enhanced.

Further, a specific embodiment of the present disclosure provides a microorganism expressing the active D-proline reductase, in which activities of one or more proteins selected from the group consisting of PrdC, PrdG, and PrdF are enhanced, in addition to the microorganism expressing the active D-proline reductase, in which the activities of PrdA protein, PrdB protein, and PrdH protein are enhanced.

The "PrdD protein, PrdE protein, $PrdE_2$ protein, PrdC protein, PrdG protein, and PrdF protein" refer to a protein constituting Prd operon of D-proline reductase. Specifically, proteins constituting Prd operon, in addition to PrdA and PrdB protein constituting D-proline reductase, are known as $PrdDEE_2CGFR$. The most well-known prd operon is present in a *Clostridium sticklandii* strain, and the protein name is based on the construction of operon (NCBI GenBank: FP565809.1) of *C. sticklandii* (Jackson et al., J. Bacteriol., 2006, 188, 8487-8495).

Functions of the proteins constituting Prd operon have not been clarified, and PrdD, PrdE, and $PrdE_2$ proteins have high sequence homology or identity to PrdA protein. Among them, PrdD protein has high sequence homology or identity to beta-PrdA protein, and PrdE and $PrdE_2$ proteins have high homology or identity to alpha-PrdA protein. Sequences of the PrdD, PrdE, and $PrdE_2$ proteins may be available from GenBank of NCBI, which is a public database. In the present disclosure, PrdD, PrdE, and $PrdE_2$ proteins may be PrdD, PrdE, and $PrdE_2$ proteins derived from *Peptoclostridium difficile* 630 (*Clostridium difficile* 630)), and specifically, they may be proteins having amino acid sequences of SEQ ID NOS: 7, 9, and 11 or amino acid sequences encoded by polynucleotide sequences of SEQ ID NOS: 8, 10, and 12, respectively, but are not limited thereto.

It is reported that PrdC protein is involved in transferring electrons to D-proline reductase by utilizing NADH (Fonknechten et al., BMC Genomics, 2010, 11, 555). PrdG protein is known as a membrane protein, but its function has not been reported. A sequence of the PrdC protein may be available from GenBank of NCBI, which is a public database. In the present disclosure, PrdC and PrdG proteins may be PrdC and PrdG proteins derived from *Peptoclostridium difficile* 630 (*Clostridium difficile* 630)), and specifically, they may be proteins having amino acid sequences of SEQ ID NOS: 13 and 15 or amino acid sequences encoded by polynucleotide sequences of SEQ ID NOS: 14 and 16, respectively, but are not limited thereto.

Further, PrdF protein which is a proline racemase is known to be involved in formation of an optical isomer of proline, and PrdR protein is reported to have functions associated with activation of prd operon (Bouillaut et al., J. Bacteriol., 2013, 195(4), 844-854). A sequence of the PrdF protein may be available from GenBank of NCBI, which is a public database. In the present disclosure, PrdF protein may be PrdF protein derived from *Peptoclostridium difficile* 630 (*Clostridium difficile* 630)), and specifically, it may be a protein having an amino acid sequence of SEQ ID NO: 17 or an amino acid sequence encoded by a polynucleotide sequence of SEQ ID NO: 18, but is not limited thereto.

As used herein, the term 'microorganism' expressing the active D-proline reductase' refers a microorganism expressing the active D-proline reductase consisting of pyruvoyl group-bound alpha-PrdA, obtained by precise self-cleavage of PrdA protein, beta-PrdA, and PrdB. The 'microorganism' may include any one of prokaryotic microorganisms and eukaryotic microorganisms, as long as it is able to produce the active D-proline reductase. For example, the microorganism may include microorganisms of the genus *Escherichia*, the genus *Erwinia*, the genus *Serratia*, the genus *Providencia*, the genus *Corynebacterium*, and the genus *Brevibacterium*. Example of the microorganism of the genus *Escherichia* may be *E. coli*, but is not limited thereto.

The active D-proline reductase-producing microorganism of the genus *Escherichia*, which is able to express the polypeptide having the D-proline reductase activity of the present disclosure, may include all microorganisms capable of expressing the polypeptide by various known methods, in addition to the above vector introduction.

Another aspect of the present disclosure provides a method of producing the active D-proline reductase, the method including the steps of culturing the microorganism expressing the active D-proline reductase in a medium, and recovering the active D-proline reductase from the microorganism or the medium.

The 'microorganism expressing the active D-proline reductase' is the same as described above.

The "culturing" means growing the microorganism under moderately controlled environmental conditions. The culturing process of the present disclosure may be performed according to an appropriate medium and culture conditions known in the art. This culturing process may be easily adjusted and used by those skilled in the art according to the strain selected. The step of culturing the microorganism may be, but is not particularly limited to, performed by known batch culture, continuous culture, fed-batch culture, etc. In this regard, the culture conditions are not particularly limited, but an optimal pH (e.g., pH 5 to 9, specifically pH 6 to 8, and most specifically pH 6.8) may be adjusted by using a basic compound (e.g., sodium hydroxide, potassium hydroxide, or ammonia) or acidic compound (e.g., phosphoric acid or sulfuric acid). Also, an antifoaming agent such as fatty acid polyglycol ester may be used during culture to suppress foam generation. To maintain the culture in an aerobic state, oxygen or oxygen-containing gas may be injected into the culture. To maintain the culture in an anaerobic or microaerobic state, no gas may be injected or nitrogen, hydrogen, or carbon dioxide gas may be injected into the culture. The culture temperature may be maintained at 20° C. to 45° C., and specifically at 25° C. to 40° C., but is not limited thereto. The culturing may be continued until a desired amount of the desired material is obtained, and specifically for about 10 hours to about 160 hours, but is not limited thereto. Additionally, in the culture medium to be used, carbon sources, such as sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid), may be used individually or in a mixture thereof, but are not limited thereto. Nitrogen sources, such as nitrogen-containing organic compounds (e.g., peptone, yeast extract, meat juice, malt extract, corn steep liquor, soybean flour, and urea) or inorganic compounds (e.g., ammonium sulfate, ammonium chloride, ammonium phosphate, ammonium carbonate, and ammonium nitrate), may be used individually or in a mixture thereof, but are not limited thereto. Potassium sources, such as potassium dihydrogen phosphate, dipotassium hydrogen phosphate, or sodium-containing salts corresponding thereto, may be used individually or in a mixture thereof, but are not limited thereto. Additionally, other essential growth-stimulating substances including metal salts (e.g., magnesium sulfate or iron sulfate), amino acids, and vitamins may be included in the medium.

The method of producing the active D-proline reductase may be readily determined by those skilled in the art under an optimized medium and culture conditions known in the art. The step of recovering the active D-proline reductase may be performed using an appropriate method known in the art. For example, centrifugation, filtration, distillation, ion exchange chromatography, crystallization, HPLC, etc., may be used, but is not limited thereto, Further, the recovery step may include a purification process, and may be performed using an appropriate method known in the art. Therefore, the active D-proline reductase to be collected may be a purified form or a fermentation broth of the microorganism including the active D-proline reductase.

Still another aspect of the present disclosure provides a method of converting D-proline or an analog thereof by a reduction method using the microorganism expressing the active D-proline reductase or the active D-proline reductase produced therefrom.

Specifically, the method may be a method of producing one or more selected from the group consisting of 5-aminovaleric acid (5-AVA), γ-aminobutyric acid (GABA), and 5-amino-4-hydroxypentanoic acid using the microorganism expressing the active D-proline reductase or the active D-proline reductase produced therefrom.

The D-proline analog is a substance having a similar structure to D-proline, and includes all analogs, in which a carboxyl group, alpha carbon, and an amino group are sequentially connected, and a ring structure including the alpha carbon and the amino group is formed, regardless of the size of the ring, and which may be reduced by the active D-proline reductase of the present disclosure. Specifically, the D-proline analog may be selected from the group consisting of D-azetidine-2-carboxylic acid, trans-4-hydroxy-D-proline, and cis-4-hydroxy-D-proline, but is not limited thereto.

Further, the reduction by the active D-proline reductase means that the bond between the alpha carbon and the amino group in the structure of D-proline or the analog thereof is broken and as a result, the ring structure is released. Specifically, D-proline may be converted into 5-aminovaleric acid (5-AVA) by the active D-proline reductase. Further, D-azetidine-2-carboxylic acid has a 4-membered ring structure due to lack of one carbon atom, compared to D-proline, and when converted by the active D-proline reductase, γ-aminobutyric acid (GABA) may be produced. Further, when cis-4-hydroxy-D-proline or trans-4-hydroxy-D-proline which is formed by adding a hydroxyl group (—OH) to the ring structure of D-proline is subjected to a conversion reaction by the active D-proline reductase, 5-amino-4-hydroxypentanoic acid may be produced, but is not limited thereto.

Still another aspect provides PrdH protein having activity to convert inactive D-proline reductase into active D-proline reductase while being co-expressed with PrdA protein and PrdB protein.

The 'PrdA protein', the 'PrdB protein', the 'PrdH protein', and the 'active D-proline reductase' are the same as described above.

As used herein, the term 'co-expressing' means that expression of two or more proteins or expression of genes encoding two or more proteins occurs at the same time. A method of expressing the gene or the protein may be readily determined from known methods in the art by those skilled in the art.

As used herein, the term "converting inactive D-proline reductase into active D-proline reductase" means that D-proline reductase in an inactive state is converted to have activity of active D-proline reductase. It means that the inactive D-proline reductase is converted into the active D-proline reductase consisting of pyruvoyl group-bound alpha-PrdA obtained by precise self-cleavage of PrdA protein, beta-PrdA, and PrdB. The 'inactive D-proline reductase' means D-proline reductase in which self-cleavage of PrdA protein does not occur, or even though self-cleavage of PrdA protein occurs, alpha-PrdA, to which no pyruvoyl group is bound, and beta-PrdA are included, or the protein of PrdA or PrdB is not expressed, or the protein of PrdA or PrdB has no activity even though expressed.

Still another aspect provides a method of producing the microorganism expressing the active D-proline reductase, the method including the steps of transforming a host cell with an expression cassette including prdA gene or prdA and prdH genes and transforming the host cell with an expression cassette including prdB gene or prdB and prdH genes.

The 'PrdA protein', the 'PrdB protein', the 'PrdH protein', the 'expression cassette', the 'active D-proline reductase', and the 'microorganism expressing the active D-proline reductase' are the same as described above.

MODE FOR INVENTION

Hereinafter, the present disclosure will be described in more detail with reference to Examples. However, these Examples are only for illustrating the present disclosure, and the scope of the present disclosure is not intended to be limited by these Examples.

Example 1: Expression of PrdA and PrdH Proteins 1-1: Gene Selection for PrdA Protein Expression For expression of PrdA protein, an experiment was performed for an amino acid sequence (Q17ZY9, UniProtKB, SEQ ID NO: 3) of D-proline reductase PrdA protein derived from *Peptoclostridium difficile* 630 (*Clostridium difficile* 630) which is known as a representative strain having Stickland reaction. A nucleotide sequence (CD630_32440, NCBI GeneBank AM180355.1, SEQ ID NO: 4) of the D-proline reductase PrdA protein was used to construct an expression vector.

1-2: Construction of PrdA-Expressing Vector (pETDuet_H6-prdA-H6)

A 6X histidine tag (H6) for Western blot analysis was incorporated to both termini of the nucleotide sequence, and a gene having NdeI and XhoI restriction enzyme sequences at the amino and carboxyl termini, respectively was synthesized. The synthesized gene and a pETDuet-1 vector were specifically digested with NdeI/XhoI restriction enzymes, respectively and then each gene fragment was obtained through separation on an agarose gel. Through enzymatic reaction of T4 ligase, a PrdA-expressing vector (pETDuet_H6-prdA-H6) was constructed.

1-3: Construction of Expression Vector having Site-Directed Mutation in Self-Cleavage Site of PrdA Protein (pETDuet_H6-prdA(C421A)-H6)

An alanine scanning method was applied to an amino acid at position 421 which is known as a site where self-cleavage of PrdA protein occurs. To perform substitution (C421A) of alanine for cysteine which is the amino acid at position 421, site-directed mutagenesis was performed. To this end, the constructed pETDuet_H6-prdA-H6 vector and primers of SEQ ID NOS: 25 and 26 (Table 1) designed for C421A mutation were added to a Pfu PCR premix to amplify the gene. At this time, PCR reaction was performed for 30 cycles of denaturation at 94° C. for 1 minute, annealing at 55° C. for 1 minute, and elongation at 72° C. for 10 minutes. This PCR product was treated with DpnI (37° C., 3 hours) and transformed into E. coli (DH5α). The transformed E. coli was cultured to obtain the strain, and a plasmid vector was isolated therefrom. Sequencing was performed to obtain a pETDuet_H6-prdA(C421A)-H6 vector.

TABLE 1

| SEQ ID NO. | Primer | Sequence (5'-3') |
|---|---|---|
| 25 | PrdA(C421A)-F | GGTATCCATGCATTAACT<u>GCC</u>ATAGGACCTGCATC AAAAG |
| 26 | PrdA(C421A)-R | CTTTTGATGCAGGTCCTAT<u>GGC</u>AGTTAATGCAT GGA TAC C |

*underlined: C421A mutation site 1-4: Construction of Expression Vector Co-Expressing PrdA and PrdH Proteins (pETDuet_prdH_H6-prdA-H6)

To induce self-cleavage of PrdA protein, it was tried to co-express a novel protein (amino acid sequence: Q17ZY5, UniProtKB, SEQ ID NO: 1/nucleotide sequence: CD630_32430, NCBI GeneBank AM180355.1, SEQ ID NO: 2; hereinafter, referred to as PrdH protein) encoded by using gene ORF present between genes encoding PrdA and PrdB which are structural proteins among proteins constituting prd operon derived from *Peptoclostridium difficile* 630 (*Clostridium difficile* 630). To this end, a gene having restriction enzyme sequences of NcoI/NotI combination each at the amino and carboxyl termini of the nucleotide sequence was synthesized. The synthesized prdH gene and the previously constructed pETDuet_H6-prdA-H6 vector were specifically digested with NcoI/NotI restriction enzymes, respectively and then each gene fragment was obtained through separation on an agarose gel. Through enzymatic reaction of T4 ligase, an expression vector (pETDuet_prdH_H6-prdA-H6) capable of co-expressing PrdA and PrdH proteins was constructed.

1-5: Identification of PrdA Protein Expression by Constructed Three Kinds of Expression Vectors and Self-Cleavage of PrdA In the next step, the constructed pETDuet_H6-prdA-H6, pETDuet_H6-prdA(C421A)-H6, or pETDuet_prdH_H6-prdA-H6 expression vector was transformed into E. coli BL21(DE3), and then seeded in an LB medium (50 ml) containing an ampicillin antibiotic (0.1 mg/ml), followed by incubation under conditions of 37° C. and 200 rpm.

To induce overexpression of the desired protein, when $OD_{600}$ value reached 0.5~0.6, 0.1 mM isopropyl β-D-1-thiogalactopyranoside (hereinafter, referred to as IPTG) was added.

Further, for the purpose of inducing self-cleavage of PrdA protein through binding of a substrate, E. coli transformed with the pETDuet_H6-prdA-H6 vector was cultured in a medium in the presence or absence of the substrate D-proline (10 mM).

Thereafter, culturing was further performed for 16 hours at 30° C. under a shaking condition of 200 rpm or at 30° C. under a stationary culture condition, respectively. The stationary culture condition was performed by omitting a shaking process to reduce non-specific degradation of the expressed PrdA protein.

To examine expression of the recombinant PrdA protein, the obtained strain was disrupted, and centrifugation (15000 rpm, 4° C., and 10 minutes) was performed to separate a supernatant, followed by SDS-PAGE analysis and Western blot analysis. As a result of the analysis, it was confirmed that the desired protein having a molecular weight of 67.6 kDa equal to a theoretical molecular weight of PrdA protein was expressed (FIG. 2). However, the protein was expressed in the form of pro-PrdA protein which was not self-cleaved, which is an inactive form of PrdA protein. For this reason, no additional protein production (alpha-PrdA, 21.9 kDa and beta-PrdA, 44.7 kDa) was found. Further, non-specifically cleaved protein bands were found in the result of Western blotting, indicating that a lot of protein degradation occurred due to structural instability of the pro-PrdA protein which was not self-cleaved (FIG. 2, lane 2). Further, the expression patterns of the PrdA(C421A) variant protein which was prepared by substituting alanine for cysteine at position 421 of PrdA protein, which is known as a self-cleavage-occurring site, were identical to those of the wild-type PrdA, also confirming that self-cleavage did not occur by the independent mechanism of PrdA protein (FIG. 2, lane 3). Further, when D-proline was added (FIG. 2, lane 4) to induce self-cleavage of PrdA protein through substrate binding or PrdA protein was co-expressed with PrdH protein, self-cleavage of PrdA protein did not occur (FIG. 2, lane 5).

When PrdA protein was expressed alone, stationary culture was performed without a shaking process in order to reduce non-specific degradation of the expressed protein, and expression patterns of PrdA protein were analyzed. In this case, degradation of the protein itself was improved due to a relatively low expression level thereof, but self-cleavage did not occur (FIG. 3, lanes 3 and 4). In detail, a cleaved protein having a similar size to the beta-PrdA protein was found, but alpha-PrdA protein was not found, indicating that the cleaved protein is a protein produced by non-specific cleavage. These results were consistent with the results of the prior art (Korean Patent Publication No. 2015-0029526; Bednarski et al., Eur. J. Biochem., 2001, 268, 3538-3544).

Example 2: Expression of PrdB Protein 2-1: Gene Selection for PrdB Protein Expression For PrdB protein expression, an experiment was performed for an amino acid sequence (Q17ZY6, UniProtKB, SEQ ID NO: 5) of D-proline reductase PrdB protein derived from *Peptoclostridium difficile* 630 (*Clostridium difficile* 630) which is known as a representative strain having Stickland reaction. A nucleotide sequence (CD630_32410, NCBI GeneBank AM180355.1, SEQ ID NO: 6) of the protein was used to construct an expression vector.

2-2: Construction of PrdB Expression Vector (pCDFDuet_prdB-H6)

A gene was synthesized by incorporating 6X histidine tag (H6) for Western blot analysis to the carboxyl terminus of the nucleotide sequence and by including NdeI and XhoI restriction enzyme sequences at the amino and carboxyl termini, respectively. The synthesized gene and a pCDF-Duet-1 vector were specifically digested with NdeI/XhoI restriction enzymes, respectively and then each gene fragment was obtained through separation on an agarose gel.

Through enzymatic reaction of T4 ligase, a PrdB-expressing vector (pCDFDuet_prdB-H6) was constructed.

2-3: Construction of Vector for Introducing Selenocysteine into PrdB Protein

PrdB protein is known as a selenoprotein. In other words, since selenocysteine is included in the amino acid sequence of PrdB protein, and the selenocysteine is a non-natural amino acid, there is a technical limitation in that the introduction through a general protein synthesis process is difficult. Therefore, in the present disclosure, selenocysteine introduction of PrdB protein was tried through introduction of a sel operon system (selABC) which is a known technique (Su et al., Nucleic Acids Res., 2005, 33(8), 2486-2492).

2-3-1: SelAB-Introduced Vector (pACYCDuet_selB/pACYCDuet_selA_selB)

To this end, SelA protein (amino acid sequence: Q18212, UniProtKB/nucleotide sequence: CD630_24950, NCBI GeneBank AM180355.1) and SelB protein (amino acid sequence: Q18210, UniProtKB/nucleotide sequence: CD630_24930, NCBI GeneBank AM180355.1) derived from *Peptoclostridium difficile* 630 (*Clostridium difficile* 630) were used, and a gene was synthesized such that it had restriction enzyme sequences of NcoI/NotI and NdeI/XhoI combination at the amino and carboxyl termini, respectively.

Next, a commercially available pACYCDuet-1 plasmid vector (Novagene) and selB gene were treated with a combination of NdeI/XhoI restriction enzymes, respectively and separated on an agarose gel. Then, through T4 ligase reaction, a pACYCDuet_selB vector was constructed. selA gene was inserted into the vector (pACYCDuet_selB) through additional restriction enzyme reaction of NdeI/XhoI combination. Finally, a pACYCDuet_selA_selB vector was constructed.

2-3-2: selC-Introduced Vector (pCDFDuet_prdB-H6_P$_{selC}$-selC)

selC gene encodes selenocysteine-specific tRNA, and was synthesized by including selC gene (nucleotide sequence: CDIF630_02727, NCBI GeneBank CP010905.1) derived from *Peptoclostridium difficile* 630 (*Clostridium difficile* 630) and additional 150 nucleotides from the amino terminus and 250 nucleotides from the carboxyl terminus such that intrinsic promoter and terminator of selC were included, and finally XbaI restriction enzyme sequence at both ends. The selC gene thus obtained and the pCDFDuet_prdB-H6 vector previously constructed were treated with XbaI restriction enzyme, and then separated on an agarose gel. Through T4 ligase reaction, a pCDFDuet_prdB-H6_P$_{selC}$-selC vector was finally constructed.

2-4: Identification of PrdB Protein Expression by Constructed Three Kinds of Expression Vectors 1) Single expression of PrdB protein The pCDFDuet_prdB-H6 vector prepared in Example 2-2 was transformed into *E. coli* BL21(DE3), and cultured in an LB medium (50 ml) containing an antibiotic (50 μg/ml of spectinomycin) (37° C., 200 rpm).

2) Co-expression of PrdB protein and selC

The pCDFDuet_prdB-H6-P$_{selC}$-selC vector prepared in Example 2-3 was transformed into *E. coli* BL21(DE3), and cultured in the same manner as in 1).

3) Co-expression of PrdB protein and selAB protein

A combination of the pCDFDuet_prdB-H6 prepared in Example 2-2 and the pACYCDuet_selA_selB vector prepared in Example 2-3 was transformed into *E. coli* BL21 (DE3), and cultured in the same manner as in 1).

4) Co-expression of PrdB protein and selABC

A combination of the pCDFDuet_prdB-H6-P$_{selC}$_selC and pACYCDuet_selA_selB vectors prepared in Example 2-3 was transformed into *E. coli* BL21(DE3), and cultured in the same manner as in 1).

To induce overexpression of the desired proteins, when OD$_{600}$ value reached 0.5~0.6, 0.1 mM IPTG was added. Further, to supply selenium needed for biosynthesis and introduction of selenocysteine, 10 μM sodium selenite was supplied or not, and then further cultured for 16 hours. Each of the obtained *E. coli* strains was disrupted, and centrifugation was performed to isolate each supernatant, followed by Western blot analysis.

As a result of the analysis, when the PrdB protein was singly expressed, PrdB protein was expressed at a very low level due to low introduction efficiency of selenocysteine (FIG. 4, lanes 1 and 2), and when PrdB protein and selC were co-expressed (FIG. 4, lanes 3 and 4) or when PrdB and SelAB proteins were co-expressed (FIG. 4, lanes 5 and 6), the same results were observed (FIG. 4). However, when PrdB protein and selABC gene were co-expressed, the expression level of PrdB protein was remarkably increased (FIG. 4, lane 7), indicating that a non-natural amino acid selenocysteine was efficiently incorporated into PrdB protein due to the effects of SelA and SelB proteins constituting sel operon and SelC which is selenocysteine-specific tRNA. Further, addition of sodium selenite (FIG. 4, lane 8; final concentration: 10 μM) further increased the expression level of PrdB protein, as compared with non-addition (lane 7), indicating that the construction of the system for efficient selenocysteine incorporation is a major factor for increasing the expression level of PrdB protein.

Example 3: Verification of Function of PrdH Protein and Evaluation of D-Proline Reductase Activity Including PrdH Protein Expression 3-1: Expression of D-Proline Reductase Protein for Verification of PrdH Function Based on the information as confirmed above, expression of D-proline reductase was tried, and to this end, the following combinations of the vectors were evaluated.

1) Co-Expression of PrdA and PrdB Proteins

Co-expression of the previously constructed PrdA protein-expressing vector (pETDuet_H6-prdA-H6) and PrdB protein-expressing vector (combination of pCDFDuet_prdB-H6-P$_{selC}$_selC and pACYCDuet_selA_selB vectors) was performed. The three kinds of the expression vectors were transformed into *E. coli* BL21(DE3), and cultured in an LB medium (50 ml) containing antibiotics (0.1 mg/ml of ampicillin, 50 μg/ml of spectinomycin, and 30 μg/ml of chloramphenicol) (37° C., 200 rpm).

2) Co-Expression of PrdA, PrdB Protein and PrdH Protein

Co-expression of the previously constructed PrdA and PrdH-co-expressing vector (pETDuet_prdH_H6-prdA-H6) and the PrdB protein-expressing vector (combination of pCDFDuet_prdB-H6-P$_{selC}$_selC and pACYCDuet_selA_selB vectors) was performed. A culturing method was performed in the same manner as in 1).

3) Co-Expression of PrdA(C421A), PrdB Protein and PrdH Protein

Co-expression of the previously constructed PrdA (C421A) protein and PrdH protein-co-expressing vector (pETDuet_prdH_H6-prdA(C421A)-H6) and the PrdB protein-expressing vector (combination of pCDFDuet_prdB-H6-P$_{selC}$_selC and pACYCDuet_selA_selB vectors) was performed. A culturing method was performed in the same manner as in 1) and 2).

To induce overexpression of the desired proteins, when $OD_{600}$ value of the culture medium reached 0.5~0.6, 0.1 mM IPTG was added to each culture medium. 10 μM sodium selenite was supplied, and then further cultured for 16 hours.

3-2: Identification of Self-Cleavage of PrdA Protein by Introduction of PrdH Protein—Western Blot Analysis The *E. coli* cells of each culture medium obtained in Example 3-1 was disrupted, and centrifugation was performed to isolate a supernatant, followed by Western blot analysis.

As a result of the analysis, when only PrdA protein and PrdB protein were co-expressed, no self-cleavage phenomenon of PrdA protein was observed (FIG. 5, lane 1). However, when PrdH protein and PrdA and PrdB proteins were co-expressed, the inactive form of PrdA protein (Pro-PrdA protein) disappeared while an additional protein band was formed (FIG. 5, lane 2).

To confirm whether or not the above experimental result was attributed to the intrinsic self-cleavage mechanism of the PrdA protein, cysteine at position 421 which is known as the self-cleavage site of PrdA protein was substituted with alanine (C421A) and co-expression of the PrdB and PrdH proteins was performed. As a result, Pro-PrdA protein was maintained while no cleaved proteins were observed (FIG. 5, lane 3), indicating that proteins additionally appeared are those resulting from specific cleavage of cysteine at the position 421 of PrdA protein.

Therefore, it was confirmed that PrdH protein is an essential protein for self-cleavage of PrdA protein, and is an auxiliary protein that plays an important role in securing the activity of PrdA protein.

In addition, based on the results of the previous Examples, in which no self-cleavage of PrdA protein occurred even though the PrdA protein and the PrdH protein were co-expressed (Example 1; FIG. 2, lane 5), it was confirmed that PrdH protein and PrdB protein must exist at the same time to induce self-cleavage of PrdA protein, indicating that PrdA protein and PrdB protein preferentially form a complex at a predetermined level or more, and then the cleavage process by PrdH protein occurs.

3-3: Evaluation of Activity of PrdH Protein-Co-Expressed D-Proline Reductase—TLC Analysis

*E. coli* cells obtained in 3-1 were adjusted to a final OD of 50, followed by centrifugation. After primary washing, *E. coli* cells were diluted with 1 mL of 0.1 M phosphate buffer (pH 8.0). Next, each 200 ul of the diluted samples was dispensed, and DTT (final concentration of 25 mM) and D-proline (final concentration of 10 mM) were added and allowed to react for 6 hours, followed by TLC analysis.

The strain co-expressing PrdA, PrdB, and PrdH proteins showed formation of a spot corresponding to 5-aminovaleric acid (5-AVA) on TLC (FIG. 6, lane 1). In the absence of PrdH protein, no activity was observed (FIG. 6, lane 2), indicating that no self-cleavage of PrdA protein occurred due to the absence of PrdH protein, and as a result, the activity of D-proline reductase was not observed.

The strain co-expressing PrdA, PrdB, and PrdH proteins was designated as CC04-9007, and then deposited at the Korean Culture Center of Microorganisms (KCCM) which is the international depository authority under the Budapest Treaty on Feb. 2, 2017 with the Accession No. KCCM11963P.

Example 4. Verification of Universal Application of PrdH Protein 4-1: Strain Selection for Verification of Universal Application of PrdH Protein To verify that the PrdH protein is an essential accessory protein universally applied to the self-cleavage of PrdA protein, it was examined whether or not PrdH protein (hereinafter, referred to as LsPrdH) was involved in the self-cleavage of PrdA protein (hereinafter, referred to as LsPrdA) derived from *Lactobacillus salivarius* which is a strain known to have the Stickland reaction, in addition to *Peptoclostridium difficile* 630.

4-2: Construction of LsPrdA-Expressing Vector (pETDuet_H6-LsprdA-H6)

A gene was synthesized by incorporating a 6× histidine tag (H6) for Western blot analysis to both termini of the nucleotide sequence of LsPrdA protein (amino acid sequence: E1JLY6, UniProtKB, SEQ ID NO: 19/nucleotide sequence: HMPREF9269_1797, NCBI GeneBank AEBA01000066.1, SEQ ID NO: 20), and by including NdeI and XhoI restriction enzyme sequences at the amino and carboxyl termini, respectively. A pETDuet-1 vector and the synthesized gene were digested with a combination of NdeI/XhoI restriction enzymes, and then each gene fragment was obtained through separation on an agarose gel. Through enzymatic reaction of T4 ligase, a pETDuet_H6-LsprdA-H6-expressing vector was constructed.

4-3: Construction of LsPrdA and LsPrdH Proteins-Co-Expressing Vector (pETDuet_LsprdH_H6-LsprdA-H6)

Additionally, restriction enzyme sequences of NcoI/NotI combination were added at both termini of a nucleotide sequence of LsPrdH protein (amino acid sequence: E1JLY7, UniProtKB, SEQ ID NO: 23/nucleotide sequence: HMPREF9269_1798, NCBI GeneBank AEBA01000066.1, SEQ ID NO: 24) and then synthesis was performed. The constructed pETDuet_H6-LsPrdA-H6-expressing vector was digested with a combination of NcoI/NotI restriction enzymes, and gene fragments were obtained through separation on an agarose gel. Through enzymatic reaction of T4 ligase, a pETDuet_LsprdH_H6-LsprdA-H6-expressing vector was constructed.

4-4: Construction of LsPrdB-Expressing Vector (pCDF-Duet_LsprdB(U151C)-H6)

A 6× histidine tag (H6) for Western blot analysis was incorporated to the carboxyl terminus of the corresponding gene of *Lactobacillus salivarius*-derived PrdB (hereinafter, referred to as LsPrdB) protein (amino acid sequence: E1JLY8 and E1JLY9, UniProtKB, SEQ ID NO: 21/nucleotide sequence: HMPREF9269_1799 and HMPREF9269_1800, NCBI GeneBank AEBA01000066.1, SEQ ID NO: 22; on the sequence database, a stop codon (UAG) sequence present in the LsPrdB protein was recognized not as a sequence for selenocysteine introduction but as a stop codon for protein expression, and thus the sequence was expressed as two protein or nucleotide sequences. Therefore, the expression vector was constructed by estimating all of the two nucleotide sequences and the sequence between the two nucleotide sequences as a nucleotide sequence of LsPrdB protein.). Further, not to recognize the codon (UGA) of selenocysteine introduced for efficient expression of PrdB protein as the stop codon, the codon was substituted with cysteine codon (UGT), and the sequences of NdeI and XhoI restriction enzymes were added at the amino and carboxyl termini, respectively.

Based on this, the pCDFDuet-1 vector and the synthesized gene were digested with a combination of NdeI/XhoI restriction enzymes, respectively and then each gene fragment was obtained through separation on an agarose gel, and through enzymatic reaction of T4 ligase, a pCDFDuet_LsprdB(U151C)-H6-expressing vector was constructed.

4-5: Identification of Self-Cleavage of LsPrdA Protein by Introduction of LsPrdH Protein—Western Blot Analysis Co-expression of a combination of the constructed LsPrdA protein-expressing vector (pETDuet_H6-LsprdA-H6) and the LsPrdB protein-expressing vector (pCDFDuet_LsprdB(U151C)-H6), or the LsPrdA and LsPrdH protein-expressing vector (pETDuet_LsprdH_H6-LsprdA-H6) and the LsPrdB protein-expressing vector (pCDFDuet_LsprdB(U151C)-H6) was performed. The two combinations of the expression vectors were transformed into E. coli BL21 (DE3), respectively and cultured in an LB medium containing antibiotics (0.1 mg/ml of ampicillin, 50 μg/ml of spectinomycin) (37° C., 200 rpm). To induce overexpression of the desired proteins, when $OD_{600}$ value reached 0.5~0.6, 0.1 mM IPTG was added, and then further cultured for 16 hours. Each of the obtained E. coli strains was disrupted, and centrifugation was performed to isolate each supernatant, followed by Western blot analysis.

As a result of the experiment, when the LsPrdA protein and the LsPrdB(U151C) protein were co-expressed, a non-cleaved form of LsPrdA protein (Pro-LsPrdA protein) and LsPrdB protein were expressed, and non-specific degradation of LsPrdA protein was observed (FIG. 7, lane 1). In contrast, when co-expressed with LsPrdH protein, Pro-LsPrdA protein was reduced while an additional protein band was observed, indicating the self-cleavage phenomenon of LsPrdA protein (FIG. 7, lane 2). LsPrdH protein has about 55% amino acid sequence homology to the PrdH protein previously obtained, but has the same characteristic in that they are encoded by the gene ORF located between the prdA gene and prdB gene on the genome.

Accordingly, it was confirmed that the two proteins (PrdH and LsPrdH protein) present at the similar position on the genome have the same function even though they have the relatively low level of sequence homology, and also confirmed that, irrespective of the kind of the strain and the sequence homology, the PrdH protein has the universal function to induce the self-cleavage of PrdA protein which is an essential step for the production of the active D-proline reductase.

Example 5: Evaluation of Activity of D-proline Reductase Operon Fully Expressed Protein—Co-Expression with $PrdDEE_2$ Protein To evaluate effects of proteins in other prd operons on the D-proline reductase of which activity was confirmed, additional co-expression was performed. As a first step, co-expression of $PrdDEE_2$ proteins was performed.

5-1: Construction of PrdA, PrdH, and $PrdDEE_2$ Proteins-Co-Expressing Vector (pETDuet_prdH_prdADEE$_2$)

To co-express each of the genes of Peptoclostridium difficile 630 (Clostridium difficile 630)-derived PrdD protein (amino acid sequence: Q17ZY7, UniProtKB, SEQ ID NO: 7/nucleotide sequence: CD630_32400, NCBI GeneBank AM180355.1, SEQ ID NO: 8), PrdE protein (amino acid sequence: Q17ZY2, UniProtKB, SEQ ID NO:9/nucleotide sequence: CD630_32390, NCBI GeneBank AM180355.1, SEQ ID NO:10), and $PrdE_2$ protein (amino acid sequence: Q17ZY3, UniProtKB, SEQ ID NO: 11/nucleotide sequence: CD630_32380, NCBI GeneBank AM180355.1, SEQ ID NO: 12) with PrdA protein, a ribosome binding site was added between the respective genes, and restriction enzyme sequences of NdeI/XhoI combination were added to both termini to perform synthesis ($prdADEE_2$). In detail, the pETDuet_prdH_H6-prdA-H6-expressing vector previously constructed in Example 1-4 and the synthesized $prdDEE_2$ gene were digested with the combination of restriction enzymes NdeI/XhoI, and then gene fragments were obtained through separation on an agarose gel. Through enzymatic reaction of T4 ligase, a pETDuet_prdH_prdADEE$_2$-expressing vector was constructed.

5-2: Co-Expression of PrdA, PrdB, PrdH and $PrdDEE_2$ Proteins and Verification of Enhanced D-Proline Reductase Activity-TLC Analysis Co-expression of PrdADEE$_2$ and PrdH proteins-expressing vector (pETDuet_prdH_prdADEE$_2$) and PrdB protein-expressing vector (combination of pCDFDuet_prdB-$P_{selC}$_selC and pACYCDuet_selA_selB vectors) was performed.

The three kinds of the expression vectors were transformed into E. coli BL21(DE3), and cultured in an LB medium containing antibiotics (0.1 mg/ml of ampicillin, 50 μg/ml of spectinomycin, and 30 μg/ml of chloramphenicol) (37° C., 200 rpm). To induce overexpression of the desired proteins, when $OD_{600}$ value reached 0.5~0.6, 01 mM IPTG was added, and 10 μM of sodium selenite was supplied, and then further cultured for 16 hours. The obtained E. coli cells were adjusted to a final OD of 50, followed by centrifugation. After primary washing, E. coli cells were diluted with 1 mL of 0.1 M phosphate buffer (pH 8.0).

Next, each 200 ul of the diluted samples was dispensed, and DTT (final concentration of 25 mM) and D-proline (final concentration of 10 mM) were added and allowed to react for 6 hours, followed by TLC analysis.

As a result, the combination with PrdAHBDEE$_2$ showed a relatively large spot of 5-aminovaleric acid on TLC, as compared with the combination with PrdAHB protein, and an initial reaction rate of the D-proline reductase was also fast (FIG. 6, lane 3). These results indicate that PrdDEE$_2$ protein induced the enhancement of D-proline reductase activity.

Example 6: Additional Expression of PrdC Protein and Verification of Enhanced D-Proline Reductase Activity Next, co-expression of PrdC protein was performed. It is known that D-proline reductase performs the conversion reaction by consuming NADH, and PrdC is involved in the NADH-dependent electron transfer. Therefore, PrdC protein may contribute to the electron transfer of D-proline reductase. To examine the effect of PrdC protein, experiments were performed in the presence or absence of a reducing agent DTT.

6-1: Construction of PrdC Protein-Expressing Vector (pACYCDuet_selA-prdC_selB)

To add a gene of Peptoclostridium difficile 630 (Clostridium difficile 630)-derived PrdC protein (amino acid sequence: Q17ZZ2, UniProtKB, SEQ ID NO: 13/nucleotide sequence: CD630_32470, NCBI GeneBank AM180355.1, SEQ ID NO: 14) to the existing D-proline reductase expression system, a vector capable of co-expressing SelA and SelB proteins was constructed. A ribosome binding site was inserted between selA and prdC genes, and restriction enzyme sequences of NcoI/NotI combination were added at both termini to perform synthesis (selA-prdC). The previously constructed pACYCDuet_selA_selB-expressing vector and the synthesized selA-prdC gene were digested with the combination of NcoI/NotI restriction enzymes, respectively and each gene fragment was obtained through separation on an agarose gel. Through enzymatic reaction of T4 ligase, a pACYCDuet_selA-prdC_selB-expressing vector was constructed.

6-2: Co-Expression of PrdA, PrdB, PrdH, and PrdC Proteins and Verification of Enhanced D-Proline Reductase Activity-TLC Analysis Co-expression of PrdADEE$_2$ and PrdH proteins-expressing vector (pETDuet_prdH_prdADEE$_2$) and PrdB and PrdC proteins-expressing vector (combination of pCDFDuet_prdB-P$_{selC}$_selC and pACYCDuet_selA-prdC_selB vectors) was performed.

The three kinds of the expression vectors were transformed into *E. coli* BL21(DE3), and cultured in an LB medium containing antibiotics (0.1 mg/ml of ampicillin, 50 μg/ml of spectinomycin, and 30 μg/ml of chloramphenicol) (37° C., 200 rpm). To induce overexpression of the desired proteins, when OD$_{600}$ value reached 0.5~0.6, 01 mM IPTG was added, and 10 μM of sodium selenite was supplied, and then further cultured for 16 hours. The obtained *E. coli* cells were adjusted to a final OD of 50, followed by centrifugation. After primary washing, *E. coli* cells were diluted with 1 mL of 0.1 M phosphate buffer (pH 8.0). As a control group thereof, *E. coli* in which PrdADEE$_2$ and PrdH proteins-expressing vector (pETDuet_prdH_prdADEE2) and PrdB protein-expressing vector (combination of pCDFDuet_prdB-P$_{selC}$_selC and pACYCDuet_selA_selB vectors) of Example 5 were co-expressed was used. Next, each 200 ul of the diluted samples was dispensed, and D-proline (final concentration of 10 mM) was added, and allowed to react in the presence or absence of DTT (final concentration of 25 mM) for 6 hours, followed by TLC analysis.

As a result of the reaction, a relatively low reaction rate was observed, as compared with addition of DTT. However, when only the PrdC protein was present, D-proline was converted into 5-aminovaleric acid even in the absence of DTT (FIG. 8, lane 2). These results indicate that the PrdC protein contributes to electron transfer of D-proline reductase, and the conversion reaction was possible by using a reducing power of intracellular NADH without addition of the reducing agent (DTT).

Example 7: Additional Expression of prdG Protein and Verification of Enhanced D-Proline Reductase Activity It is estimated that PrdG protein is a membrane protein, but there has been no report of the accurate function thereof until now.

7-1: Construction of PrdG and PrdB Proteins-Co-Expressing Vector (pCDFDuet_prdG_prdB-P$_{selC}$_selC)

A gene was synthesized by including restriction enzyme sequences of NcoI/NotI combination at the amino and carboxyl termini of a nucleotide sequence of *Peptoclostridium difficile* 630 (*Clostridium difficile* 630)-derived PrdG protein (amino acid sequence: Q17ZY0, UniProtKB, SEQ ID NO: 15/nucleotide sequence: CD630_32360, NCBI GeneBank AM180355.1; it was not named PrdG protein on the sequence database, but named PrdG protein herein, based on homology to PrdG protein of *C. sticklandii*, SEQ ID NO: 16). The synthesized prdG gene and the previously constructed pCDFDuet_prdB-P$_{selC}$_selC vector were digested with NcoI/NotI restriction enzymes, and then each gene fragment was obtained through separation on an agarose gel. Through enzymatic reaction of T4 ligase, a PrdG protein and PrdB protein-co-expressing vector (pCDFDuet_prdG_prdB-P$_{selC}$_selC) was constructed.

7-2: Co-Expression of PrdA, PrdB, PrdH and PrdCG Proteins and Verification of Enhanced D-Proline Reductase Activity-TLC Analysis Co-expression of a combination of PrdA and PrdH protein-expressing vector (pETDuet_prdH_prdA) and PrdB protein-expressing vector (pCDFDuet_prdB-P$_{selC}$_selC and pACYCDuet_selA_selB), or a combination of PrdA and PrdH protein-expressing vector (pETDuet_prdH_prdA) and PrdB and PrdCG protein-co-expressing vector (pCDFDuet_prdG_prdB-P$_{selC}$_selC and pACYCDuet_selA-prdC_selB) was performed.

The three kinds of the expression vectors were transformed into *E. coli* BL21(DE3), and cultured in an LB medium containing antibiotics (0.1 mg/ml of ampicillin, 50 μg/ml of spectinomycin, and 30 μg/ml of chloramphenicol) (37° C., 200 rpm). To induce overexpression of the desired proteins, when OD$_{600}$ value reached 0.5~0.6, 01 mM IPTG was added, and 10 μM of sodium selenite was supplied, and then further cultured for 16 hours. The obtained *E. coli* cells were adjusted to a final OD of 50, followed by centrifugation. After primary washing, *E. coli* cells were diluted with 1 mL of 0.1 M phosphate buffer (pH 8.0).

Considering that PrdG protein is a membrane protein, each 200 ul of the diluted samples of PrdAHB combination and PrdAHBCG combination was dispensed, and D-proline (final concentration of 10 mM) was added, and the whole cells, cell lysates under the same OD condition, and supernatants thereof obtained by centrifugation were allowed to react in the presence or absence of DTT (final concentration of 25 mM) and in the presence or absence of 1% glucose for 6 hours, followed by TLC analysis.

As a result of the experiment, when the PrdAHBCG combination additionally including the PrdC protein exhibited activity with or without DTT (FIG. 9, wo, lanes 4 to 6), and in particular, when DTT was added to the supernatant of the cell lysate and allowed to react, the PrdAHBCG combination showed a relatively low level of activity, as compared with the PrdAHB combination (FIG. 9, DTT, lane 6).

These results indicate that a significant portion of the expressed D-proline reductase was removed by centrifugation, and due to binding with the PrdG protein having the membrane protein characteristic, the expressed D-proline reductase was removed after precipitation by centrifugation. Further, in the DTT-based conversion reaction, both PrdAHB and PrdAHBCG combinations showed similar levels of activity in the whole cells and the cell lysates. When 1% glucose was added to increase NADH supply without DTT, only the PrdAHBCG combination showed activity (FIG. 9, 1% glucose). Based on the experimental results of Example 6 showing that PrdC protein is related with NADH availability, it can be seen that through association with PrdC protein, PrdG protein induces formation of the D-proline reductase complex which readily utilizes intracellular NADH. In other words, when a reducing agent such as DTT is used, it is possible to directly transfer electrons to D-proline reductase with or without a mediator protein. However, when intracellular NADH is used without externally adding the reducing agent, the mediator protein (PrdC protein) capable of helping the electron transfer is needed, and for the construction of an efficient electron transfer system, PrdG protein functions to increase integration of D-proline reductase, thereby inducing the effect of improving the activity.

Example 8: Preparation of Strain Producing 5-Aminovaleric Acid from D-Proline Using Auxiliary Protein PrdH

8-1: Preparation of Strain Producing 5-Aminovaleric Acid

To produce 5-aminovaleric acid from a sugar source by a microorganism, it is required to supply D-proline which is a substrate of D-proline reductase. However, since *E. coli* has no D-proline biosynthesis pathway, a metabolic pathway of using D-proline which is converted from L-proline was designed. In detail, proline racemase having a proline isomer-forming ability must exist at the same time. Therefore, in the present disclosure, an experiment was performed through introduction of proline racemase which is the known technique (Rudnick et al., Biochemistry, 1975, 14(20), 4515-4522).

To this end, to insert the gene prdF of *Peptoclostridium difficile* 630 (*Clostridium difficile* 630)-derived proline racemase protein (amino acid sequence: Q17ZY4, UniProtKB, SEQ ID NO: 17/nucleotide sequence: CD630_32370, NCBI GeneBank AM180355.1, SEQ ID NO: 18) into the existing D-proline reductase expression system, a ribosome binding site was added between the respective genes for co-expression with PrdG protein, and then restriction enzyme sequences of NcoI/NotI combination were added to both termini to perform synthesis (prdGF).

The previously constructed pCDFDuet_prdG_prdB-$P_{selC}$_selC expression vector and the synthesized prdGF gene were digested with the combination of NcoI/NotI restriction enzymes, and each gene fragment was obtained through separation on an agarose gel. Through enzymatic reaction of T4 ligase, a pCDFDuet_prdGF_prdB-$P_{selC}$_selC-expressing vector was constructed.

8-2: Verification of Production of 5-Aminovaleric Acid by Active D-Proline Reductase-LC/MS and TLC Analysis A combination of PrdA and PrdH proteins-expressing vector (pETDuet_prdH_prdA) and PrdBCG (pCDFDuet_prdG_prdB-$P_{selC}$_selC and pACYCDuet_selA-prdC_selB vectors), and a combination of PrdA and PrdH proteins-expressing vector (pETDuet_prdH_prdA) and PrdBCGF protein-expressing vector (pCDFDuet_prdGF_prdB-$P_{selC}$_selC and pACYCDuet_selA-prdC_selB vectors) were expressed. The two combinations of the expression vectors were transformed into *E. coli* BL21(DE3), and cultured in an LB medium containing antibiotics (0.1 mg/ml of ampicillin, 50 µg/ml of spectinomycin, and 30 µg/ml of chloramphenicol) (37° C., 200 rpm). To induce overexpression of the desired proteins, when $OD_{600}$ value reached 0.5~0.6, 0.1 mM IPTG was added, and 10 µM of sodium selenite and 1% glucose (NADH enhanced) were supplied, and then further cultured at 30° C., 200 rpm for 24 hours. The culture media obtained by centrifugation was subjected to LC/MS and TLC analysis.

As a result of the experiment, about 67.7 ppm of 5-aminovaleric acid was produced in the presence of proline racemase (FIG. 10, lane 3), and 5-aminovaleric acid was not produced in the absence of proline racemase (FIG. 10, lanes 1 to 2). In other words, it was confirmed that L-proline was produced from the added sugar source through a metabolism in *E. coli*, and then converted into D-proline by proline racemase, and finally, 5-aminovaleric acid was produced by the introduced active D-proline reductase.

8-3: Production of 5-Aminovaleric Acid from D-Proline Added to Culture Medium In addition to a process of producing 5-aminovaleric acid from a sugar source by direct fermentation, an experiment was performed to convert 5-aminovaleric acid from D-proline which was externally added during culturing the microorganism including the active D-proline reductase.

In detail, an experiment was performed to examine whether or not 5-aminovaleric acid may be biosynthesized from D-proline added to a culture medium. To this end, the previously constructed PrdA and PrdH proteins-expressing vector (pETDuet_prdH_prdA) and PrdBCG protein-expressing vector (combination of pCDFDuet_prdG_prdB-$P_{selC}$_selC and pACYCDuet_selA-prdC_selB vector) were co-expressed. The three kinds of the expression vectors were transformed into *E. coli* BL21(DE3), and cultured in an LB medium containing antibiotics (0.1 mg/ml of ampicillin, 50 µg/ml of spectinomycin, and 30 µg/ml of chloramphenicol) (37° C., 200 rpm). To induce overexpression of the desired proteins, when $OD_{600}$ value reached 0.5~0.6, 01 mM IPTG was added, and 10 µM of sodium selenite and 1% glucose were supplied, and then further cultured at 30° C., 200 rpm for 24 hours in the presence or absence of 5 mM D-proline. The culture medium obtained by centrifugation was subjected to LC/MS analysis.

As a result of the analysis, it was confirmed that 5-aminovaleric acid was not observed in the absence of D-proline, whereas 196.7 ppm (1.68 mM) of 5-aminovaleric acid on average was produced in the presence of 5 mM of D-proline, which was confirmed by HPLC (Shimadzu) analysis.

Example 9: Evaluation of D-Proline Analog Substrate Based on D-Proline Reductase To further confirm the activity of the constructed active D-proline reductase, various substrates other than proline were subjected to the conversion reaction. In this Example, D-azetidine-2-carboxylic acid (D-Aze) having a similar structure to D-proline, cis-4-hydroxy-D-proline and trans-4-hydroxy-D-proline, in which a hydroxyl group (—OH) was added to the ring structure of D-proline, were used as substrates of the D-proline reductase.

To this end, the previously constructed PrdA and PrdH proteins-expressing vector (pETDuet_prdH_prdA) and PrdB protein-expressing vector (combination of pCDFDuet_prdB-$P_{selC}$_selC and pACYCDuet_selA_selB vector) were co-expressed. The three kinds of the expression vectors were transformed into *E. coli* BL21(DE3), and cultured in an LB medium containing antibiotics (0.1 mg/ml of ampicillin, 50 µg/ml of spectinomycin, and 30 µg/ml of chloramphenicol) (37° C., 200 rpm). To induce overexpression of the desired proteins, when $OD_{600}$ value reached 0.5~0.6, 01 mM IPTG was added, and 10 µM of sodium selenite was supplied, and then further cultured for 16 hours. The obtained *E. coli* cells were adjusted to a final OD of 50, followed by centrifugation. After primary washing, *E. coli* cells were diluted with 1 mL of 0.1 M phosphate buffer (pH 8.0). Next, each 200 ul of the diluted samples was dispensed, and DTT (final concentration of 25 mM) and various substrates (final concentration of 10 mM, FIG. 11A) were added and allowed to react for 6 hours, followed by TLC analysis. D-azetidine-2-carboxylic acid has a 4-membered ring structure due to lack of one carbon atom, compared to D-proline, and when converted by the D-proline reductase, γ-aminobutyric acid (GABA) is produced. As a result of the reaction, D-azetidine-2-carboxylic acid showed a relatively low reaction rate, as compared with D-proline, but GABA production was clearly observed on TLC (FIG. 11B, lane 6).

When cis-4-hydroxy-D-proline or trans-4-hydroxy-D-proline is subjected to the conversion reaction, 5-amino-4-hydroxypentanoic acid is produced. As a result of the reaction, cis-4-hydroxy-D-proline or trans-4-hydroxy-D- proline showed a relatively low reaction rate, as compared with D-proline, but substrate reduction on TLC and newly formed TLC spot were observed, irrespective of isomer form of the hydroxyl group (FIG. 11C, lane 5 and lane 8).

These results indicate that the expressed active D-proline reductase is able to convert other substrates having different sizes of the ring structure and substrate analogs having additional modification as well as the known D-proline.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. A microorganism comprising:
   (i) a first expression vector encoding PrdA protein and a second expression vector encoding PrdH protein, or
   (ii) a third expression vector encoding PrdH protein and PrdA protein, and a fourth expression vector encoding PrdB protein,
   wherein the PrdH protein comprises a polypeptide having a sequence identity of at least 90% to the amino acid sequence of SEQ ID NO: 1 or SEQ ID NO: 23, the PrdA protein comprises a polypeptide having a sequence identity of at least 80% to SEQ ID NO: 3 or SEQ ID NO: 19, and the PrdB protein comprises a polypeptide having a sequence identity of at least 80% to SEQ ID NO: 5 or SEQ ID NO: 21.

2. The microorganism of claim 1, wherein the PrdB protein comprises a polypeptide having a sequence identity of at least 85% to SEQ ID NO: 5 or SEQ ID NO: 21.

3. The microorganism of claim 1, wherein one of the expression vectors further encodes one or more proteins selected from the group consisting of PrdD, PrdE, PrdE2, PrdC, PrdG, and PrdF.

4. The microorganism of claim 1, wherein the microorganism is *E. coli*.

5. A method of producing active D-proline reductase, the method comprising the steps of:
   culturing the microorganism of claim 1 in a medium, and
   recovering the active D-proline reductase from the microorganism or the medium.

6. A method of producing one or more selected from the group consisting of aminovaleric acid (5-aminovaleric acid, 5-AVA), γ-aminobutyric acid (GABA), and 5-amino-4-hydroxypentanoic acid using the microorganism of claim 1.

7. A method of producing a microorganism expressing active D-proline reductase, the method comprising:
   transforming a host cell with a first expression cassette comprising prdA gene or prdA and prdH genes; and
   transforming the host cell with a second expression cassette comprising prdB gene or prdB and prdH genes,
   wherein the prdH gene encodes PrdH protein comprising a polypeptide having a sequence identity of at least 90% to SEQ ID NO: 1 or SEQ ID NO: 23, the prdA gene encodes PrdA protein comprising a polypeptide having a sequence identity of at least 80% to SEQ ID NO: 3 or SEQ ID NO: 19, and the prdB encodes PrdB protein comprising a polypeptide having a sequence identity of at least 80% to SEQ ID NO: 5 or SEQ ID NO: 21;
   wherein the microorganism is a microorganism of the genus *Escherichia*.

8. The method of producing the microorganism expressing active D-proline reductase of claim 7, wherein the PrdH protein comprises a polypeptide having a sequence identity of at least 95% to SEQ ID NO: 1 or SEQ ID NO: 23 and the PrdA protein comprises a polypeptide having a sequence identity of at least 85% to SEQ ID NO: 3 or SEQ ID NO: 19.

9. The method of producing the microorganism expressing active D-proline reductase of claim 7, wherein the PrdB protein comprises a polypeptide having a sequence identity of at least 85% to SEQ ID NO: 5 or SEQ ID NO: 21.

10. The method of producing the microorganism expressing active D-proline reductase of claim 7, wherein one of the expression cassettes further comprises one or more genes selected from the group consisting of prdD gene that encodes PrdD protein, prdE gene that encodes PrdE protein, prdE2 gene that encodes PrdE2 protein, prdC gene that encodes PrdC protein, prdG gene that encodes PrdG protein, and prdF gene that encodes PrdF protein.

11. The method of producing the microorganism expressing active D-proline reductase of claim 7, wherein the microorganism is *E. coli*.

12. The microorganism of claim 1, wherein the PrdH protein comprises the amino acid sequence of SEQ ID NO: 1.

13. The microorganism of claim 1, wherein the PrdH protein comprises the amino acid sequence of SEQ ID NO: 23.

14. The microorganism of claim 1, comprising the first expression vector encoding PrdA protein and the second expression vector encoding PrdH protein.

15. The microorganism of claim 1, comprising the third expression vector encoding PrdH protein and PrdA protein, and the fourth expression vector encoding PrdB protein.

16. The microorganism of claim 1, wherein the microorganism is *E. coli*, and the PrdH protein comprises a polypeptide having a sequence identity of at least 95% to the amino acid sequence of SEQ ID NO: 1 or SEQ ID NO: 23.

* * * * *